(12) United States Patent
Jeong et al.

(10) Patent No.: US 11,896,745 B2
(45) Date of Patent: Feb. 13, 2024

(54) DEODORIZATION MODULE AND STORAGE DEVICE INCLUDING DEODORIZATION MODULE

(71) Applicant: Seoul Viosys Co., Ltd., Ansan-si (KR)

(72) Inventors: Jae Hak Jeong, Ansan-si (KR); Ji Won Kim, Ansan-si (KR); Byeong Cheol Ju, Ansan-si (KR); Sang Cheol Shin, Ansan-si (KR); Woong Ki Jung, Ansan-si (KR)

(73) Assignee: Seoul Viosys Co., Ltd., Ansan-si (KR)

( * ) Notice: Subject to any disclaimer, the term of this patent is extended or adjusted under 35 U.S.C. 154(b) by 156 days.

(21) Appl. No.: 17/379,407

(22) Filed: Jul. 19, 2021

(65) Prior Publication Data

US 2022/0008609 A1 Jan. 13, 2022

Related U.S. Application Data

(63) Continuation of application No. 16/206,026, filed on Nov. 30, 2018, now Pat. No. 11,065,359, which is a
(Continued)

(30) Foreign Application Priority Data

Jun. 2, 2016 (KR) ........................ 10-2016-0069034
Jun. 15, 2016 (KR) ........................ 10-2016-0074604

(51) Int. Cl.
*A61L 9/20* (2006.01)
*F25D 17/04* (2006.01)

(52) U.S. Cl.
CPC ................. *A61L 9/205* (2013.01); *A61L 9/20* (2013.01); *F25D 17/04* (2013.01); *F25D 17/042* (2013.01);
(Continued)

(58) Field of Classification Search
CPC ........ A61L 9/205; A61L 9/20; A61L 2209/14; F25D 17/04; F25D 17/042; F25D 17/06;
(Continued)

(56) References Cited

U.S. PATENT DOCUMENTS 5,230,220 A 7/1993 Kang et al.
2007/0266725 A1 11/2007 Anikhindi et al.
(Continued)

FOREIGN PATENT DOCUMENTS

CN 201036630 Y 3/2008
JP 2001-355958 12/2001
(Continued)

OTHER PUBLICATIONS

Translation of Asano, JP2004333035A (Year: 2004).*
(Continued)

*Primary Examiner* — Sean E Conley
*Assistant Examiner* — Brendan A Hensel
(74) *Attorney, Agent, or Firm* — Oblon, McClelland, Maier & Neustadt, L.L.P.

(57) ABSTRACT

A deodorization module includes a housing having a bar securing member and a substrate securing member, and formed of a reflective material, wherein each of the bar securing member and the substrate securing member protrudes inward from an inner side surface of the housing and has a groove. A photocatalyst bar is disposed such that air introduced into the housing passes through the photocatalyst bar. A light source module including a light source substrate and an ultraviolet (UV) light source is disposed on a first surface of the light source substrate, wherein the light source module is configured to emit light toward the photocatalyst bar. An external guide protrudes outward around an outer periphery of the housing.

19 Claims, 22 Drawing Sheets

Related U.S. Application Data continuation of application No. PCT/KR2017/005397, filed on May 24, 2017.

(52) U.S. Cl.
CPC ... *A61L 2209/12* (2013.01); *F25D 2317/0415* (2013.01); *F25D 2317/0417* (2013.01); *F25D 2317/0681* (2013.01)

(58) Field of Classification Search
CPC ..... F25D 2317/0681; F25D 2317/0417; F25D 2317/0415; B01D 46/0038
See application file for complete search history.

(56) References Cited

U.S. PATENT DOCUMENTS

| | | | |
|---|---|---|---|
| 2011/0030560 A1* | 2/2011 | Bohlen | A61L 9/22 96/57 |
| 2012/0181911 A1 | 7/2012 | Kim et al. | |
| 2013/0094204 A1* | 4/2013 | Budai | A61L 9/205 362/230 |
| 2015/0033784 A1 | 2/2015 | Park et al. | |
| 2015/0059398 A1 | 3/2015 | Yoo et al. | |
| 2015/0064069 A1 | 3/2015 | Yi et al. | |
| 2017/0216475 A1 | 8/2017 | Park et al. | |
| 2017/0348456 A1 | 12/2017 | Park et al. | |

FOREIGN PATENT DOCUMENTS

| | | |
|---|---|---|
| JP | 2004-333035 | 11/2004 |
| JP | 2008-096017 | 4/2008 |
| KR | 10-2015-0014815 | 2/2015 |
| KR | 10-2015-0028163 | 3/2015 |
| KR | 10-2015-0112711 | 10/2015 |
| WO | 2014116065 | 7/2014 |

OTHER PUBLICATIONS

International Search Report dated Aug. 8, 2017, in International Application No. PCT/KR2017/005397 (with English Translation).
Extended European Search Report dated Dec. 9, 2019, issued on European Patent Application No. 17806927.4.
Non-Final Office Action dated Mar. 19, 2020, in U.S. Appl. No. 16/206,026.
Final Office Action dated Sep. 9, 2020, in U.S. Appl. No. 16/206,026.
Advisory Action dated Nov. 20, 2020, in U.S. Appl. No. 16/206,026.
Notice of Allowance dated Mar. 18, 2021, in U.S. Appl. No. 16/206,026.
European Office Action dated Aug. 18, 2023, in European Patent Application No. 17806927.4.

\* cited by examiner

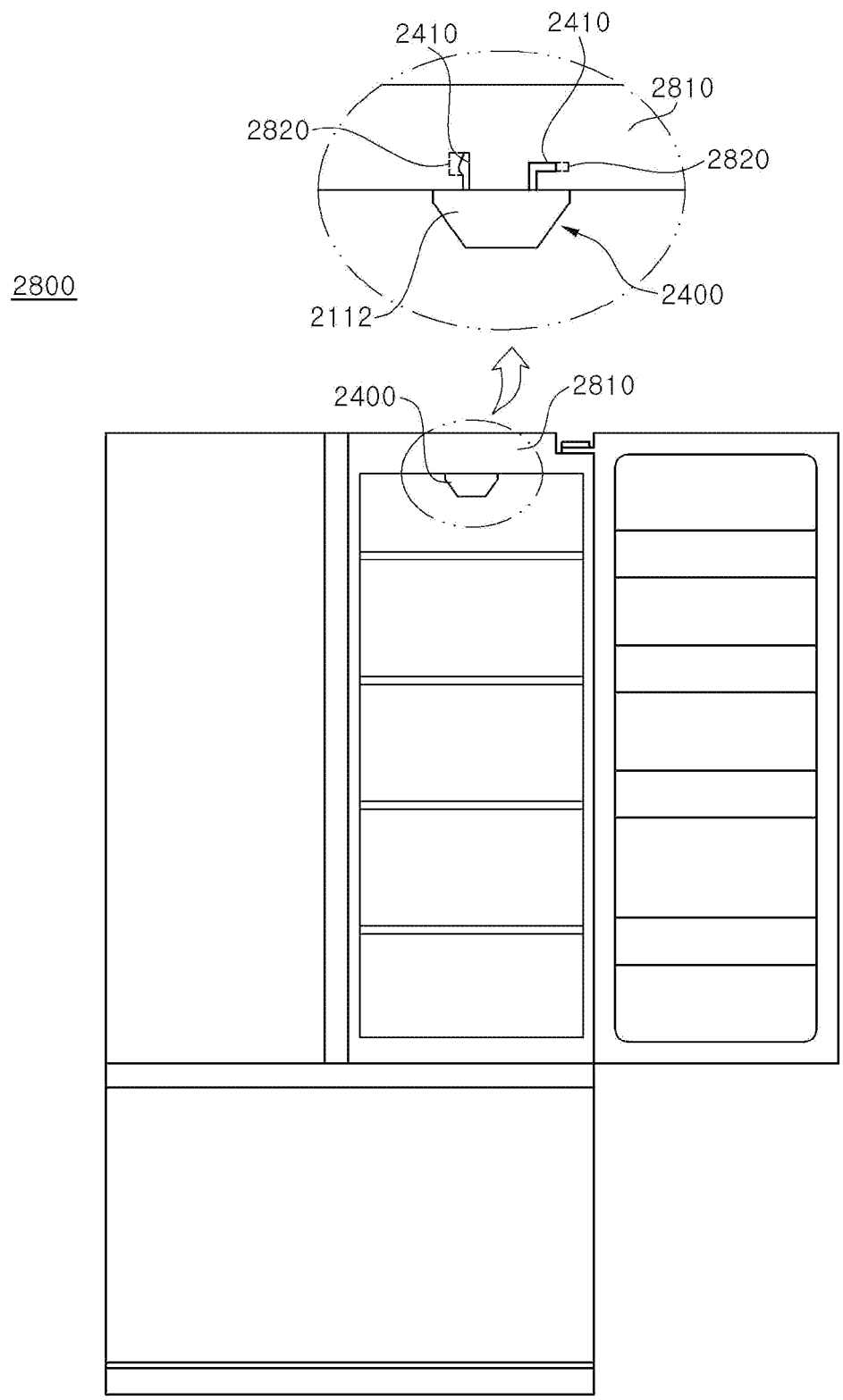

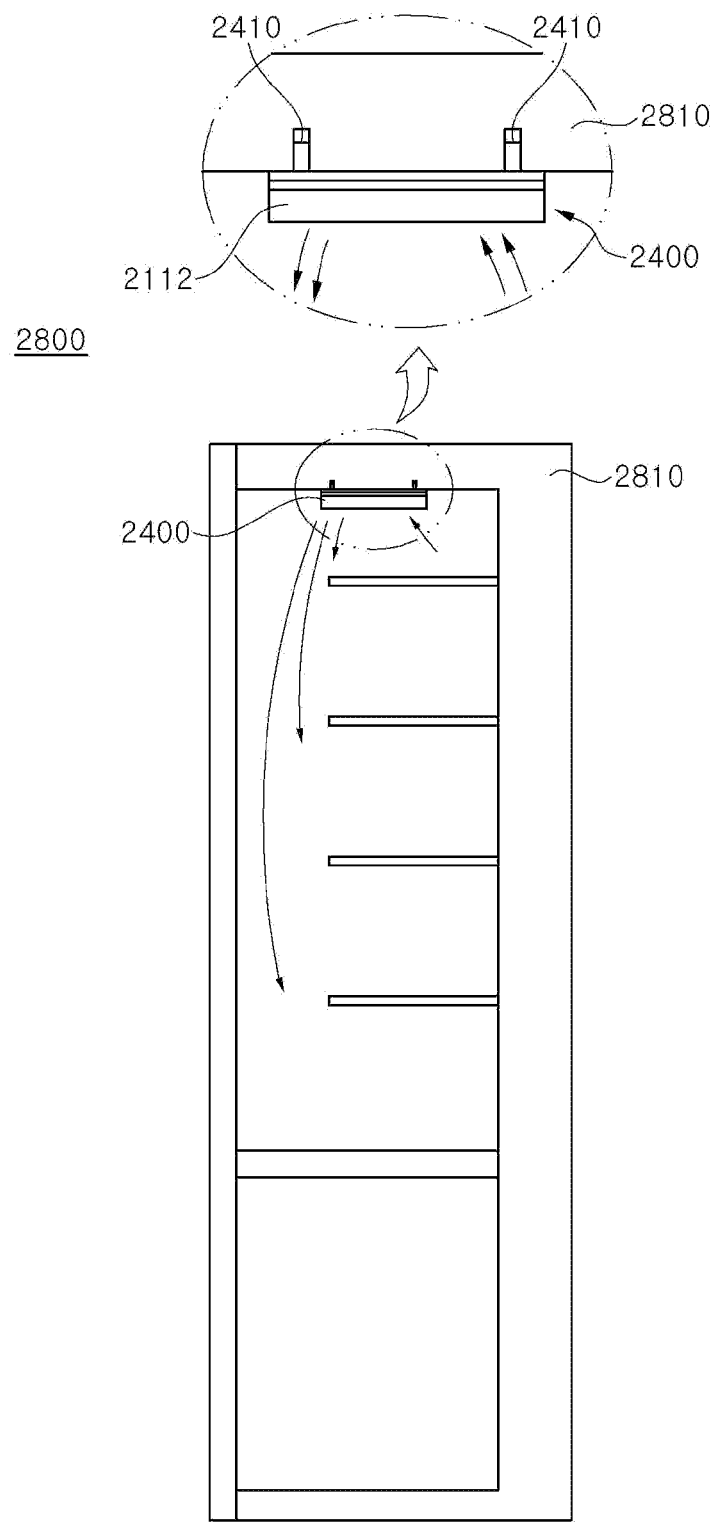

DEODORIZATION MODULE AND STORAGE DEVICE INCLUDING DEODORIZATION MODULE

CROSS REFERENCE TO RELATED APPLICATIONS

This application is a Continuation of U.S. patent application Ser. No. 16/206,026, filed Nov. 30, 2018, which is a Continuation of International Patent Application No. PCT/KR2017/005397, filed on May 24, 2017, and claims priority from and the benefit of Korean Patent Application No. 10-2016-0069034, filed on Jun. 2, 2016, and Korean Patent Application No. 10-2016-0074604, filed on Jun. 15, 2016, each of which is incorporated by reference for all purposes as if fully set forth herein.

BACKGROUND

Field

Exemplary embodiments/implementations of the disclosure relate generally to a deodorization module and a storage apparatus including the same.

Discussion of the Background

A refrigerator is used to store food for a long period of time while preventing the food from going bad. Generally, the temperature of the refrigerator is regulated within a range of 0° C. to 10° C. If food is left unattended in the refrigerator for a long enough time, the food starts to decay, smells bad, and offends a user. When a food absorbs the smell of another food, it loses its unique smell and spoils.

For this reason, most refrigerators are equipped with various deodorization apparatuses for removing the smell of food itself or the odor of decaying food, preventing circulation of the odor, and providing sterilization.

Typical deodorization apparatuses use a deodorization filter in which manganese oxide ($MnO_2$), copper oxide (CuO), an artificial enzyme catalyst and the like are supported on a lattice of activated carbon. However, such deodorization apparatuses suck in a small amount of air per unit time. In addition, an air passage inside the deodorizing device is narrow, causing partial loss of suctioned air. Further, the deodorization filter has a small area and thus cannot provide sufficient deodorization.

The above information disclosed in this Background section is only for understanding of the background of the inventive concepts, and, therefore, it may contain information that does not constitute prior art.

SUMMARY

It is one aspect of the inventive concepts to provide a deodorization module capable of deodorizing air in a storage chamber and a storage apparatus including the same.

It is another aspect of the inventive concepts to provide a deodorization module capable of deodorizing all suctioned air sucked and a storage apparatus including the same.

In accordance with an exemplary embodiment of the invention, there is provided a deodorization module including: a housing; a suction hole formed through a bottom of the housing to allow air to be sucked into the housing therethrough; a fan disposed at the suction hole to suck in air; a discharge hole allowing the air sucked in by the fan to be discharged from the housing therethrough; a photocatalyst bar disposed between the fan and the discharge hole; and a light source module including a light source substrate and an ultraviolet (UV) light source and emitting UV light toward the photocatalyst bar.

In accordance with another exemplary embodiment, a deodorization module includes: a housing; a suction hole formed through one side of the housing to allow air to be sucked into the housing therethrough; a fan disposed between the suction hole and the other side of the housing opposite the one side of the housing to suck in air; a discharge hole formed through the one side of the housing to allow the air sucked in by the fan to be discharged from the housing therethrough; a flow path connected between an air outlet of the fan and the discharge hole; a photocatalyst bar disposed in the flow path between the fan and the discharge hole; and a light source module disposed in the flow path to emit UV light toward the photocatalyst bar.

In accordance with a further exemplary embodiment, there is provided a storage apparatus including: a storage chamber having an internal space; and a deodorization module mounted on the storage chamber to deodorize air inside the storage chamber.

It is to be understood that both the foregoing general description and the following detailed description are exemplary and explanatory and are intended to provide further explanation of the invention as claimed.

BRIEF DESCRIPTION OF THE DRAWINGS

The accompanying drawings, which are included to provide a further understanding of the invention and are incorporated in and constitute a part of this specification, illustrate exemplary embodiments of the invention, and together with the description serve to explain the inventive concepts.

FIG. 29 and FIG. 30 are exemplary views of a storage apparatus according to a second exemplary embodiment of the inventive concepts.

DETAILED DESCRIPTION

Figure 1:
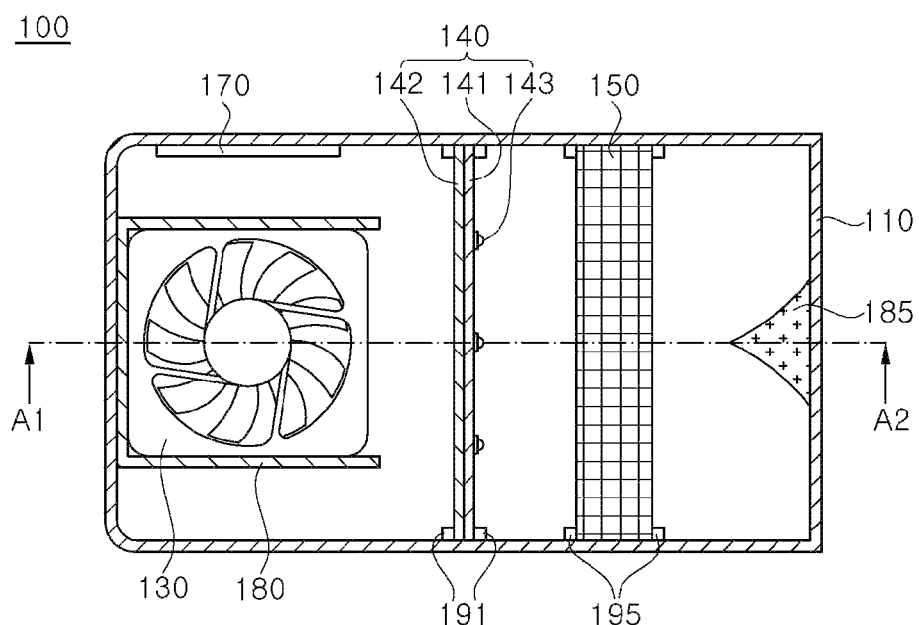
FIG. 1 is a top sectional view of a deodorization module according to a first exemplary embodiment of the inventive concepts.

In the following description, for the purposes of explanation, numerous specific details are set forth in order to provide a thorough understanding of various exemplary embodiments or implementations of implementations of the invention. As used herein "embodiments" and "implementations" are interchangeable words that are non-limiting examples of devices or methods employing one or more of the inventive concepts disclosed herein. It is apparent, however, that various exemplary embodiments may be practiced without these specific details or with one or more equivalent arrangements. In other instances, well-known structures and devices are shown in block diagram form in order to avoid unnecessarily obscuring various exemplary embodiments. Further, various exemplary embodiments may be different, but do not have to be exclusive. For example, specific shapes, configurations, and characteristics of an exemplary embodiment may be used or implemented in another exemplary embodiment without departing from the scope of the inventive concepts.

Unless otherwise specified, the illustrated exemplary embodiments are to be understood as providing exemplary features of varying detail of some ways in which the inventive concepts may be implemented in practice. Therefore, unless otherwise specified, the features, components, modules, layers, films, panels, regions, and/or aspects, etc. (hereinafter individually or collectively referred to as "elements"), of the various embodiments may be otherwise combined, separated, interchanged, and/or rearranged without departing from the scope of the inventive concepts.

The use of cross-hatching and/or shading in the accompanying drawings is generally provided to clarify boundaries between adjacent elements. As such, neither the presence nor the absence of cross-hatching or shading conveys or indicates any preference or requirement for particular materials, material properties, dimensions, proportions, commonalities between illustrated elements, and/or any other characteristic, attribute, property, etc., of the elements, unless specified. Further, in the accompanying drawings, the size and relative sizes of elements may be exaggerated for clarity and/or descriptive purposes. When an exemplary embodiment may be implemented differently, a specific process order may be performed differently from the described order. For example, two consecutively described processes may be performed substantially at the same time or performed in an order opposite to the described order. Also, like reference numerals denote like elements.

When an element, such as a layer, is referred to as being "on," "connected to," or "coupled to" another element or layer, it may be directly on, connected to, or coupled to the other element or layer or intervening elements or layers may be present. When, however, an element or layer is referred to as being "directly on," "directly connected to," or "directly coupled to" another element or layer, there are no intervening elements or layers present. To this end, the term "connected" may refer to physical, electrical, and/or fluid connection, with or without intervening elements. Further, the D1-axis, the D2-axis, and the D3-axis are not limited to three axes of a rectangular coordinate system, such as the x, y, and z-axes, and may be interpreted in a broader sense. For example, the D1-axis, the D2-axis, and the D3-axis may be perpendicular to one another, or may represent different directions that are not perpendicular to one another. For the purposes of this disclosure, "at least one of X, Y, and Z" and "at least one selected from the group consisting of X, Y, and Z" may be construed as X only, Y only, Z only, or any combination of two or more of X, Y, and Z, such as, for instance, XYZ, XYY, YZ, and ZZ. As used herein, the term "and/or" includes any and all combinations of one or more of the associated listed items.

Although the terms "first," "second," etc. may be used herein to describe various types of elements, these elements should not be limited by these terms. These terms are used to distinguish one element from another element. Thus, a first element discussed below could be termed a second element without departing from the teachings of the disclosure.

Spatially relative terms, such as "beneath," "below," "under," "lower," "above," "upper," "over," "higher," "side" (e.g., as in "sidewall"), and the like, may be used herein for descriptive purposes, and, thereby, to describe one elements relationship to another element(s) as illustrated in the drawings. Spatially relative terms are intended to encompass different orientations of an apparatus in use, operation, and/or manufacture in addition to the orientation depicted in the drawings. For example, if the apparatus in the drawings is turned over, elements described as "below" or "beneath" other elements or features would then be oriented "above" the other elements or features. Thus, the exemplary term "below" can encompass both an orientation of above and below. Furthermore, the apparatus may be otherwise oriented (e.g., rotated 90 degrees or at other orientations), and, as such, the spatially relative descriptors used herein interpreted accordingly.

The terminology used herein is for the purpose of describing particular embodiments and is not intended to be limiting. As used herein, the singular forms, "a," "an," and "the"

are intended to include the plural forms as well, unless the context clearly indicates otherwise. Moreover, the terms "comprises," "comprising," "includes," and/or "including," when used in this specification, specify the presence of stated features, integers, steps, operations, elements, components, and/or groups thereof, but do not preclude the presence or addition of one or more other features, integers, steps, operations, elements, components, and/or groups thereof. It is also noted that, as used herein, the terms "substantially," "about," and other similar terms, are used as terms of approximation and not as terms of degree, and, as such, are utilized to account for inherent deviations in measured, calculated, and/or provided values that would be recognized by one of ordinary skill in the art.

Various exemplary embodiments are described herein with reference to sectional and/or exploded illustrations that are schematic illustrations of idealized exemplary embodiments and/or intermediate structures. As such, variations from the shapes of the illustrations as a result, for example, of manufacturing techniques and/or tolerances, are to be expected. Thus, exemplary embodiments disclosed herein should not necessarily be construed as limited to the particular illustrated shapes of regions, but are to include deviations in shapes that result from, for instance, manufacturing. In this manner, regions illustrated in the drawings may be schematic in nature and the shapes of these regions may not reflect actual shapes of regions of a device and, as such, are not necessarily intended to be limiting.

As is customary in the field, some exemplary embodiments are described and illustrated in the accompanying drawings in terms of functional blocks, units, and/or modules, such as control boards and control units. Those skilled in the art will appreciate that these blocks, units, and/or modules are physically implemented by electronic (or optical) circuits, such as logic circuits, discrete components, microprocessors, hard-wired circuits, memory elements, wiring connections, and the like, which may be formed using semiconductor-based fabrication techniques or other manufacturing technologies. In the case of the blocks, units, and/or modules being implemented by microprocessors or other similar hardware, they may be programmed and controlled using software (e.g., microcode) to perform various functions discussed herein and may optionally be driven by firmware and/or software. It is also contemplated that each block, unit, and/or module may be implemented by dedicated hardware, or as a combination of dedicated hardware to perform some functions and a processor (e.g., one or more programmed microprocessors and associated circuitry) to perform other functions. Also, each block, unit, and/or module of some exemplary embodiments may be physically separated into two or more interacting and discrete blocks, units, and/or modules without departing from the scope of the inventive concepts. Further, the blocks, units, and/or modules of some exemplary embodiments may be physically combined into more complex blocks, units, and/or modules without departing from the scope of the inventive concepts.

Unless otherwise defined, all terms (including technical and scientific terms) used herein have the same meaning as commonly understood by one of ordinary skill in the art to which this disclosure is a part. Terms, such as those defined in commonly used dictionaries, should be interpreted as having a meaning that is consistent with their meaning in the context of the relevant art and should not be interpreted in an idealized or overly formal sense, unless expressly so defined herein.

According to one aspect of the inventive concepts, a deodorization module includes: a housing; a suction hole formed through a bottom of the housing to allow air to be sucked into the housing therethrough; a fan disposed at the suction hole to suck in air; a discharge hole allowing the air sucked in by the fan to be discharged from the housing therethrough; a photocatalyst bar disposed between the fan and the discharge hole; and a light source module including a light source substrate and a UV light source and emitting UV light toward the photocatalyst bar.

Since the fan is disposed at the suction hole and directly sucks in air, a large amount of air can be sucked into the deodorization module.

The photocatalyst bar may be disposed such that all of the air sucked in by the fan can pass through the photocatalyst bar. Opposite side surfaces of the photocatalyst bar may tightly contact opposite inner side surfaces of the housing, respectively; an upper surface of the photocatalyst bar may tightly contact an upper inner surface of the housing; and a lower surface of the photocatalyst bar may tightly contact a lower inner surface of the housing. That is, the entire interior of the housing provides an air flow passage. The photocatalyst bar may be formed across the entirety of the air flow passage. Accordingly, all of the air sucked into the deodorization module passes through the photocatalyst bar, whereby efficient air deodorization can be achieved.

The light source module may be disposed between the fan and the photocatalyst bar. Alternatively, the light source module may be disposed between the photocatalyst bar and a rear inner surface of the housing. Here, the light source module is spaced apart from the rear inner surface of the housing. Thus, it is possible to prevent condensation on the housing due to heat generated by the light source module.

An upper surface of the light source module may be spaced apart from an upper inner surface of the housing and a lower surface of the light source module may be spaced apart from a lower inner surface of the housing.

The light source substrate may be a metal printed circuit board. When the light source substrate is a metal printed circuit board, the deodorization module can have improved heat dissipation performance. For improvement in heat dissipation performance, the light source module may further include a heat sink.

When the light source module includes plural UV light sources, the UV light can be evenly irradiated onto the photocatalyst bar.

The discharge holes may be formed opposite side walls of the housing, respectively. In this case, the deodorization module may further include a rear discharge guide formed on a rear inner surface of the housing to guide deodorized air to the discharge holes. The rear discharge guide may be provided in the form of a triangular prism with curved sides. The rear discharge guide serves to guide deodorized air to flow to the pair of discharge holes.

The discharge hole may be formed through the bottom of the housing. In this case, the rear discharge guide may be omitted.

The deodorization module may further include a bottom discharge guide formed on a lower inner surface of the housing between the photocatalyst bar and the discharge hole. The bottom discharge guide may extend upward from the lower inner surface of the housing to below the UV light source.

The deodorization module may further include an air suction guide formed in the housing, wherein the air suction guide may be located between one side of the fan and one inner side wall of the housing and between the other side of the fan and the other inner side wall of the housing.

A portion of the bottom of the housing through which the suction hole is formed may be inclined.

The housing may be formed of a reflective material or an inner wall of the housing may be coated with a reflective material.

The deodorization module may further include a control board applying electrical power and control signals to the fan and the light source module.

The deodorization module may further include an external guide protruding outward around an outer periphery of the housing. In this case, the discharge hole may be formed below the external guide.

The housing may be divided into a main body and a cover, wherein the cover is detachably coupled to the main body. The main body has an open top and receives the suction hole, the fan, the discharge hole, the photocatalyst bar, and the light source module. The cover covers the open top of the main body.

The deodorization module may further include a cover guide formed on a lower surface of the cover. The cover guide may be gradually reduced in thickness toward the discharge hole. The cover guide may be located above the fan when the cover is coupled to the main body.

According to another aspect of the inventive concepts, a storage apparatus includes: a storage chamber having an internal space; and a deodorization module mounted on the storage chamber to deodorize air inside the storage chamber. Here, the storage chamber may be a refrigerator or a heating cabinet.

The deodorization module may be mounted on an upper side of the storage chamber.

The storage apparatus may further include a groove-shaped deodorization module mount formed on the storage chamber, such that the deodorization module is inserted into the deodorization module mount. Here, the suction hole and the discharge hole of the deodorization module may be exposed to the internal space of the storage chamber. When the deodorization module includes the external guide, an upper surface of the external guide may contact the storage chamber and a lower surface of the external guide may be exposed to the internal space of the storage chamber.

According to a further aspect of the inventive concepts, a deodorization module includes: a housing; a suction hole formed through one side of the housing to allow air to be sucked into the housing therethrough; a fan disposed between the suction hole and the other side of the housing opposite the one side of the housing to suck in air; a discharge hole formed through the one side of the housing to allow the air sucked in by the fan to be discharged from the housing therethrough; a flow path connected between an air outlet of the fan and the discharge hole; a photocatalyst bar disposed in the flow path between the fan and the discharge hole; and a light source module disposed in the flow path to emit UV light toward the photocatalyst bar.

The air sucked in by the fan passes through the photocatalyst bar before being discharged from the housing through the discharge hole. Since the fan is disposed at the suction hole and directly sucks in air, a large amount of air can be sucked into the deodorization module. In addition, use of the fan can allow suctioned air to be easily redirected.

The flow path may be defined by a flow path side wall surrounding the photocatalyst bar and the light source module. One surface of the flow path side wall may tightly contact one inner surface of the housing and the other surface of the flow path side wall may tightly contact the other inner surface of the housing opposite the one inner surface of the housing. The flow path side wall may be formed with a flow path opening connected to the air outlet of the fan. The flow path opening may have the same size as the air outlet of the fan. Accordingly, the air sucked in by the fan can be discharged to the flow path without loss.

A portion of the flow path side wall between a rear inner surface of the housing and the light source module or between the rear inner surface of the housing and the photocatalyst bar may have an inclined inner surface. That portion of the flow path side wall may be gradually reduced in thickness from the other side of the housing to the one side of the housing. With the inclined inner surface of the flow path side wall, air pressure loss due to collision of air with the flow path side wall can be reduced.

The flow path side wall may be formed of a reflective material or an inner surface of the flow path side wall may be coated with a reflective material.

The flow path may be gradually increased in width from the air outlet of the fan to a deodorization section in which the photocatalyst bar and the light source module are disposed. In addition, the flow path may be gradually reduced in width from the deodorization section to the discharge hole. That is, the deodorization section may be widest of all sections of the flow path. For example, the flow path may have an octagonal cross-section. With the flow path having this shape, the air sucked in by the fan can pass through the photocatalyst bar while spreading widely, whereby sufficient air deodorization can be achieved. However, the shape of the flow path is not limited thereto. The flow path may have a polygonal or elliptical cross-section. Alternatively, the flow path may have a cross-sectional shape composed of two straight lines and two curves connecting opposite ends of one straight line to opposite ends of the other straight line, respectively. It will be understood that the flow path may have any other suitable shape, without limitation.

Both side surfaces of the photocatalyst bar may tightly contact the flow path side wall. In addition, one surface of the photocatalyst bar may tightly contact one inner surface of the housing and the other surface of the photocatalyst bar may tightly contact the other inner surface of the housing. That is, the photocatalyst bar may be formed across the entirety of the air flow passage. Accordingly, all of the air sucked into the deodorization module passes through the photocatalyst bar, whereby efficient air deodorization can be achieved.

The deodorization module may further include a pair of bar securing members formed on opposite inner surfaces of the flow path side wall to secure the photocatalyst bar in the flow path. The pair of bar securing members may be configured to receive opposite side surfaces of the photocatalyst bar. Accordingly, the photocatalyst bar can be secured in the flow path using the pair of bar securing members.

One surface of the light source module may be spaced apart from one inner surface of the housing and the other surface of the light source module may be spaced apart from the other inner surface of the housing. The light source module may be disposed between the fan and the photocatalyst bar. Alternatively, the light source module may be disposed between the photocatalyst bar and the discharge hole.

The light source module may include a light source substrate and a UV light source. For improvement in heat dissipation performance, the light source module may further include a heat sink.

The deodorization module may further include a pair of module securing members formed at opposite inner surfaces of the flow path side wall to secure the light source module in the flow path. The pair of module securing members is configured to receive opposite side surfaces of the light source module. Accordingly, the light source module can be secured in the flow path using the pair of module securing members.

The housing may include: a main body having at least one open side and receiving the fan, the flow path, the photocatalyst bar, and the light source module; and a cover covering the open side of the main body and having the suction hole and the discharge hole formed through one side thereof, wherein the cover is detachably coupled to the main body.

The housing may further include a fastening member, wherein the fastening member protrudes outward from an outer wall of the housing and has a bent portion.

The housing may be formed of a reflective material or an inner wall of the housing may be coated with a reflective material.

The deodorization module may further include a control board applying electrical power and control signals to the fan and the light source module.

The discharge hole of the deodorization module may be disposed between the photocatalyst bar and the light source module.

According to yet another aspect of the inventive concepts, a storage apparatus includes: a storage chamber having an internal space; and a deodorization module mounted on the storage chamber to deodorize air inside the storage chamber. The deodorization module may be mounted on one side of the storage chamber.

The storage camber may have a fastening groove formed on an inner wall thereof, wherein the fastening groove is configured to receive the bent portion of the fastening member. The deodorization module is mounted on the inner wall of the storage chamber by inserting the fastening member into the fastening groove. The storage apparatus may be a refrigerator or a heating cabinet.

FIG. 1, FIG. 2, FIG. 3, and FIG. 4 are views of a deodorization module according to a first exemplary embodiment of the inventive concepts.

Figure 2:
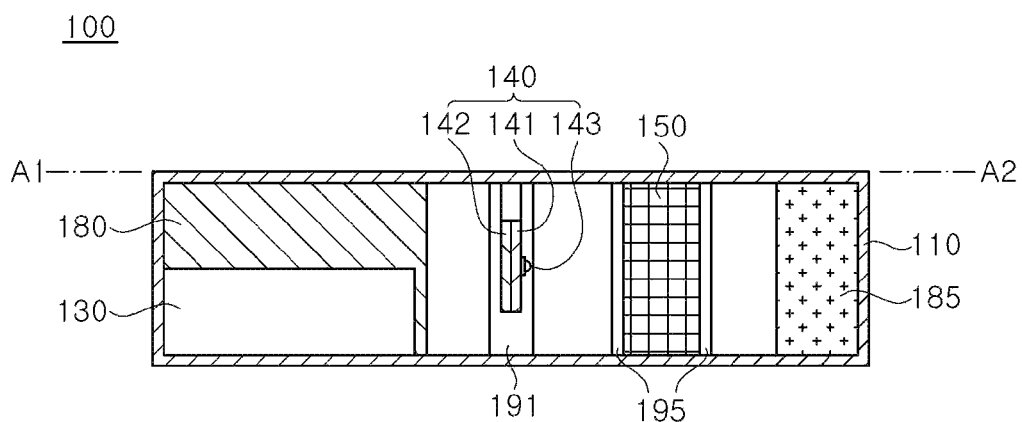
FIG. 2 is a side sectional view of the deodorization module according to the first exemplary embodiment.
Figure 3:
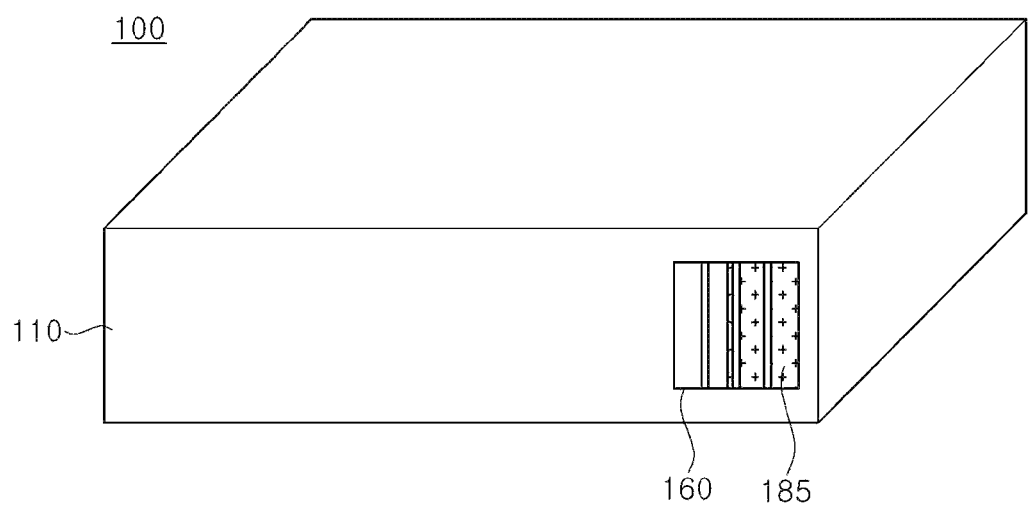
FIG. 3 is a side view of the deodorization module according to the first exemplary embodiment.
Figure 4:
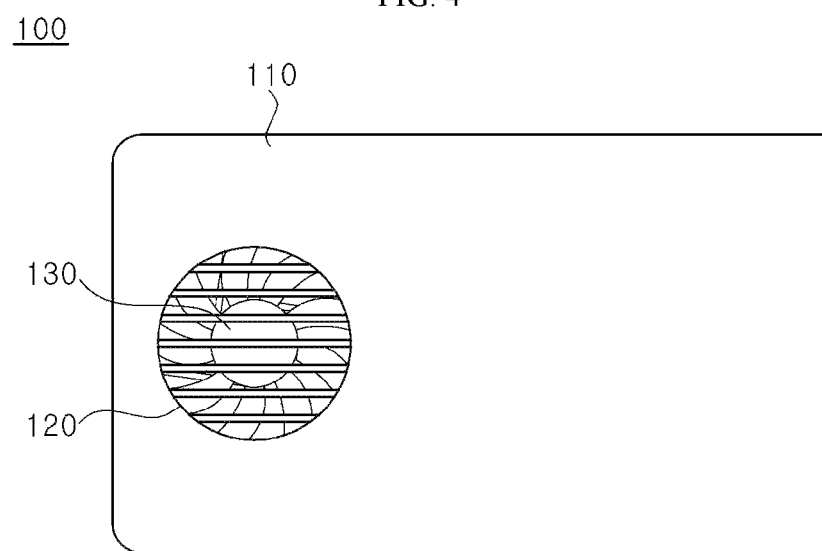
FIG. 4 is a bottom elevation view of the deodorization module according to the first exemplary embodiment.

FIG. 1 is a top sectional view of the deodorization module according to the first exemplary embodiment. FIG. 2 is a side sectional view of the deodorization module according to the first exemplary embodiment. FIG. 3 is a side view of the deodorization module according to the first exemplary embodiment. FIG. 4 is a bottom elevation view of the deodorization module according to the first exemplary embodiment.

Referring to FIG. 1 to FIG. 4, the deodorization module 100 according to the first exemplary embodiment includes a housing 110, a suction hole 120, a fan 130, a light source module 140, a photocatalyst bar 150, a discharge hole 160, and a control board 170.

In this exemplary embodiment, the housing 110 is configured to receive the fan 130, the photocatalyst bar 150, the light source module 140, and the control board 170.

The suction hole 120 is a hole through which air is sucked into the housing 110. The suction hole 120 is formed through a bottom of the housing 110. In addition, the suction hole 120 is formed in a region where the fan 130 is disposed.

A suction guide 180 may be formed at both sides of the suction hole 120. The suction guide 180 protrudes upward from a lower inner surface of the housing 110. In addition, the suction guide 180 is open between the fan 130 and the light source module 140. Thus, the suction guide 180 serves to guide the air sucked in by the fan 130 through the suction hole 120 to move to the light source module 140.

The fan 130 is disposed on the suction hole 120. Here, the fan 130 is a blower having a rotation axis parallel to the direction of a flow of air. For example, the fan 130 may be an axial flow fan. The fan 130 is disposed such that the rotation axis thereof is perpendicular to the bottom of the housing through which the suction hole 120 is formed. Thus, the fan 130 directly sucks in air outside the housing 110 through the suction hole 120 and discharges the air directly into the housing 110. In this way, the fan 130 can suck in a large amount of air at once, thereby improving deodorization efficiency.

In this exemplary embodiment, the fan 130 may be fitted into the suction guide 180 so as to be secured in the housing 110. Alternatively, the fan 130 may be coupled to the bottom of the housing 110 using a screw. It should be understood that the inventive concepts are not limited thereto and the fan 130 may be secured in the housing 110 by any suitable fastening method known in the art.

The light source module 140 is disposed between the fan 130 and the photocatalyst bar 150. The light source module 140 includes a light source substrate 141, a heat sink 142, and a UV light source 143.

The light source substrate 141 is electrically connected to the UV light source 143 and applies electric signals to the UV light source 143. For example, the light source substrate 141 may be a printed circuit board or a metal printed circuit board. When the light source substrate 141 is a metal printed circuit board, the deodorization module 100 can have improved heat dissipation performance.

Opposite side surfaces of the light source substrate 141 tightly contact opposite inner side surfaces of the housing 110, respectively. For example, the light source substrate 141 may be secured to an inner wall of the housing 110 using a pair of substrate securing members 191. The pair of substrate securing members 191 protrudes inward from the opposite inner side surfaces of the housing 110, respectively. In addition, each of the pair of substrate securing members 191 has a vertical groove formed thereon to extend from the top thereof. Here, the depth of the groove may vary depending on the height at which the light source substrate 141 is to be positioned. The light source substrate 141 is secured in the housing 110 by inserting opposite side surfaces of the light source substrate into the grooves of the pair of substrate securing members 191, respectively.

An upper side surface of the light source substrate 141 is spaced apart from an upper inner surface of the housing 110. In addition, a lower side surface of the light source substrate 141 is spaced apart from the lower inner surface of the housing 110. The spaces between the light source substrate 141 and the housing 110 provide an air flow passage. That is, air sucked in by the fan 130 moves to the photocatalyst bar 150 through the spaces above and below the light source substrate 141.

The UV light source 143 is mounted on one surface of the light source substrate 141. The UV light source 143 emits UV light toward the photocatalyst bar 150. For example, the UV light source 143 may be a light-emitting diode (LED) chip. One or more the UV light sources 143 may be mounted on the light source substrate 141. When plural UV light sources 143 are mounted on the light source substrate 141, the photocatalyst bar 150 can be evenly irradiated with UV light. The number of UV light sources 143 may be adjusted, as needed.

The heat sink 142 is disposed on the other surface of the light source substrate 141. The heat sink 142 may be attached to the other surface of the light source substrate 141 using a thermally conductive adhesive. The heat sink 142 is configured to dissipate heat from the UV light source 143 and the light source substrate 141. The heat sink 142 is formed of a thermally conductive material. For example, the heat sink 142 may be formed of a metal. In this exemplary embodiment, it has been described that the light source module 140 includes the heat sink 142. However, it should be understood that the inventive concepts are not limited thereto. That is, the heat sink 142 may be omitted, as needed. In addition, the heat sink 142 may be formed of any suitable material known in the art and may be attached to the light source substrate 141 by any suitable method known in the art.

The photocatalyst bar 150 is disposed between the light source substrate 141 and the discharge hole 160. The photocatalyst bar 150 is provided in the form of a bar having a plurality of through-holes. For example, the photocatalyst bar 150 may be formed of a porous ceramic material. Alternatively, the photocatalyst bar 150 may be formed of a metal foam including nickel (Ni), iron (Fe), aluminum (Al), chromium (Cr), and the like. A surface of the photocatalyst bar 150 may be coated with a photocatalytic material. The photocatalytic material may include at least one selected from the group consisting of $TiO_2$, $ZnO$, $ZrO_2$, and $WO_3$. Alternatively, the photocatalyst bar 150 per se may contain a photocatalytic material.

In this exemplary embodiment, UV light emitted from the UV light source 143 reacts with the photocatalytic material of the photocatalyst bar 150 to generate hydroxyl radicals (·OH). The hydroxyl radicals decompose and remove pollutants or odorous substances. That is, air sucked in by the fan 130 is deodorized in the process of passing through the through-holes of the photocatalyst bar 150.

The photocatalyst bar 150 is disposed such that all of the air sucked in by the fan 130 can pass through the photocatalyst bar 150. For example, opposite side surfaces of the photocatalyst bar 150 may tightly contact the opposite inner side surfaces of the housing 110, respectively. In addition, an upper side surface of the photocatalyst bar 150 may tightly contact the upper inner surface of the housing 110. Further, a lower side surface of the photocatalyst bar 150 may tightly contact the lower inner surface of the housing 110. Since the all side surfaces of the photocatalyst bar 150 tightly contact an inner wall of the housing 110, air sucked into the housing will necessarily pass through the photocatalyst bar 150. That is, all of the air sucked into the housing 110 is deodorized by the light source module 140 and the photocatalyst bar 150 before being discharged from the housing 110.

The photocatalyst bar 150 may be secured to the inner wall of the housing 110 using a pair of bar securing members 195. The pair of bar securing members 195 protrudes inward from the opposite inner side surfaces of the housing 110, respectively. In addition, each of the pair of bar securing members 195 has a vertical groove formed thereon to extend from the top to the bottom thereof. Thus, the photocatalyst bar 150 is secured to the inner wall of the housing 110 by inserting opposite side surfaces of the photocatalyst bar into the grooves of the pair of bar securing members 195.

In this exemplary embodiment, it has been described that the substrate securing member 191 and the bar securing member 195 are formed separately of the housing 110. However, the substrate securing member 191 and the bar securing member 195 may be integrally formed with the housing 110.

In this exemplary embodiment, the discharge hole 160 may include a pair of discharge holes respectively formed through opposite side walls of the housing 110. Here, the discharge hole 160 is formed between the photocatalyst bar 150 and a rear inner surface of the housing 110. The discharge hole 160 is a hole through which the air deodorized through the photocatalyst bar 150 is discharged to the outside.

A rear discharge guide 185 is formed on the rear inner surface of the housing 110. The rear discharge guide 185 is provided in the form of a triangular prism having curved side surfaces. One side surface of the rear discharge guide 185 contacts the housing 110 and the other two side surfaces are curved and face the two discharge holes 160, respectively. The rear discharge guide 185 guides the deodorized air to move toward the discharge hole 160.

The control board 170 applies electrical power and control signals to the fan 130 and the light source module 140. In this exemplary embodiment, the fan 130 and the light source module 140 are described as receiving electric power and control signals from a single common control board 170. However, it should be understood that the inventive concepts are not limited thereto. That is, as one alternative, the fan 130 and the light source module 140 may receive electrical power and control signals from different control boards, respectively. As another alternative, the control board 170 may be omitted and the fan 130 and the light source module 140 may directly receive electrical power and control signals from outside.

The housing 110 may be formed of a reflective material. Alternatively, the inner wall of the housing 110 may be coated with a reflective material. Here, the rear discharge guide 185 of the housing 110 may be formed of a reflective material or may be coated with a reflective material.

In the deodorization module 100 according to this exemplary embodiment, the interior of the housing 110 itself serves as an air flow passage. Accordingly, it is possible to prevent the air sucked in from being lost during movement. In addition, the photocatalyst bar 150 is formed across the air flow passage. Accordingly, all of the air sucked into the deodorization module 100 can pass through the photocatalyst bar 150. In this way, the deodorization module 100 according to this exemplary embodiment can suck in a large amount of air and thoroughly deodorize the sucked air without air loss, thereby providing efficient air deodorization.

Figure 5:
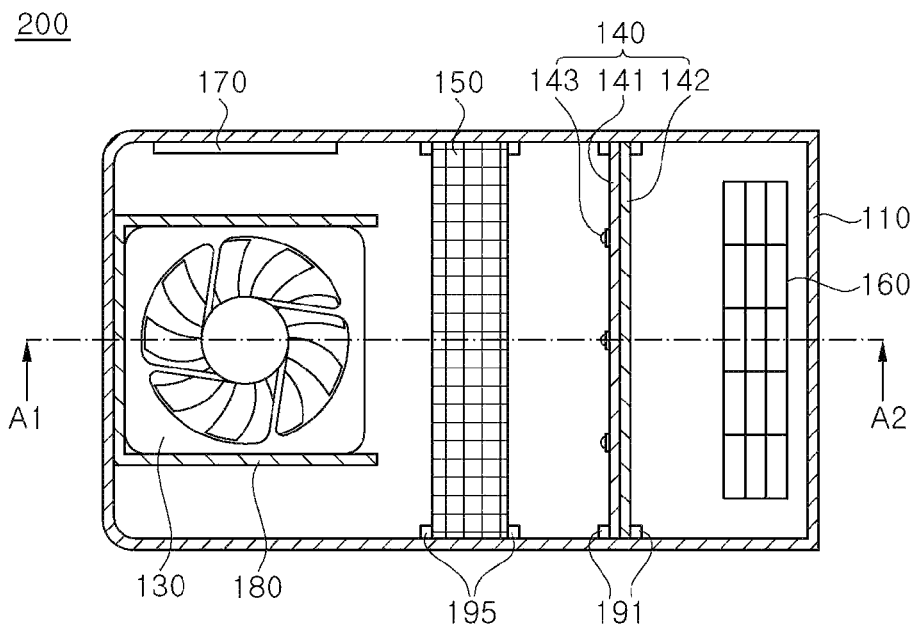
FIG. 5 is a top sectional view of a deodorization module according to a second exemplary embodiment of the inventive concepts.
Figure 6:
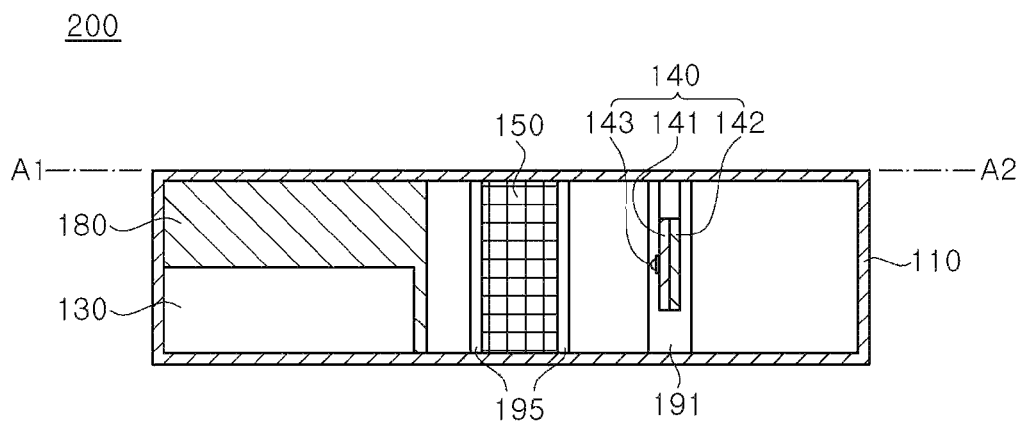
FIG. 6 is a side sectional view of the deodorization module according to the second exemplary embodiment.
Figure 7:
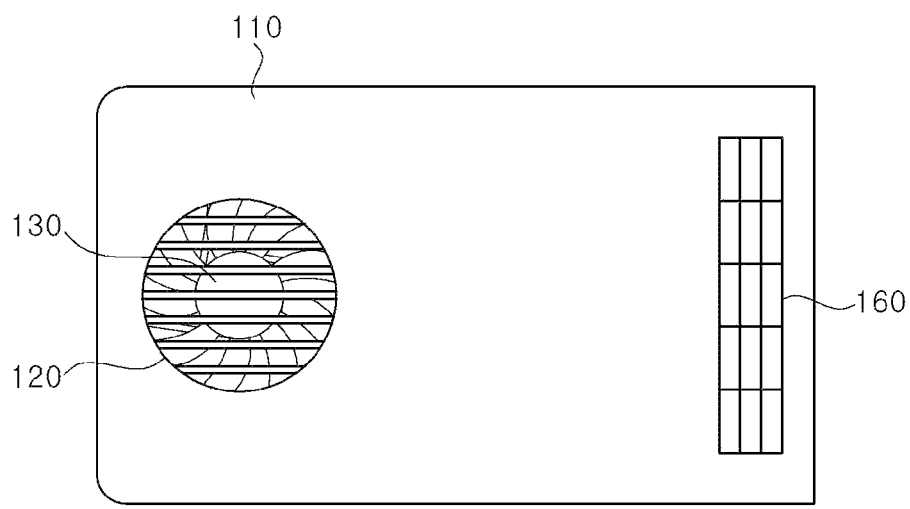
FIG. 7 is a bottom elevation view of the deodorization module according to the second exemplary embodiment.

FIG. 5 to FIG. 7 are views of a deodorization module according to a second exemplary embodiment of the inventive concepts.

FIG. 5 is a top sectional view of a deodorization module according to a second exemplary embodiment of the inventive concepts. FIG. 6 is a side sectional view of the deodorization module according to the second exemplary embodiment. FIG. 7 is a bottom elevation view of the deodorization module according to the second exemplary embodiment.

With regard to the deodorization module 200 according to the second exemplary embodiment, detailed description of the same components as those of the deodorization module 100 according to the first exemplary embodiment will be omitted. For omitted details, refer to the description with reference to FIG. 1 to FIG. 4.

In this exemplary embodiment, the photocatalyst bar 150 is disposed between the fan 130 and the light source module 140. In addition, the light source module 140 is disposed between the photocatalyst bar 150 and the discharge hole 160. The UV light source 143 of the light source module 140 emits UV light toward the photocatalyst bar 150.

Air sucked in by the fan 130 is deodorized in the process of passing through the photocatalyst bar 150. The deodorized air moves to the discharge hole 160 through spaces above and below the light source module 140.

In this exemplary embodiment, the discharge hole 160 may be formed through the bottom of the housing 110. In addition, the discharge hole 160 is located between the light source module 140 and the rear inner surface of the housing 110. When the discharge hole 160 is formed through the bottom surface of the housing 110, the deodorized air can be more easily discharged outside the housing 110 than when the discharge hole 160 is formed on the side wall of the housing 110. When the discharge hole 160 is formed through the bottom of the housing 110, as in this exemplary embodiment, the rear discharge guide 185 according to the first exemplary embodiment may be omitted.

Figure 8:
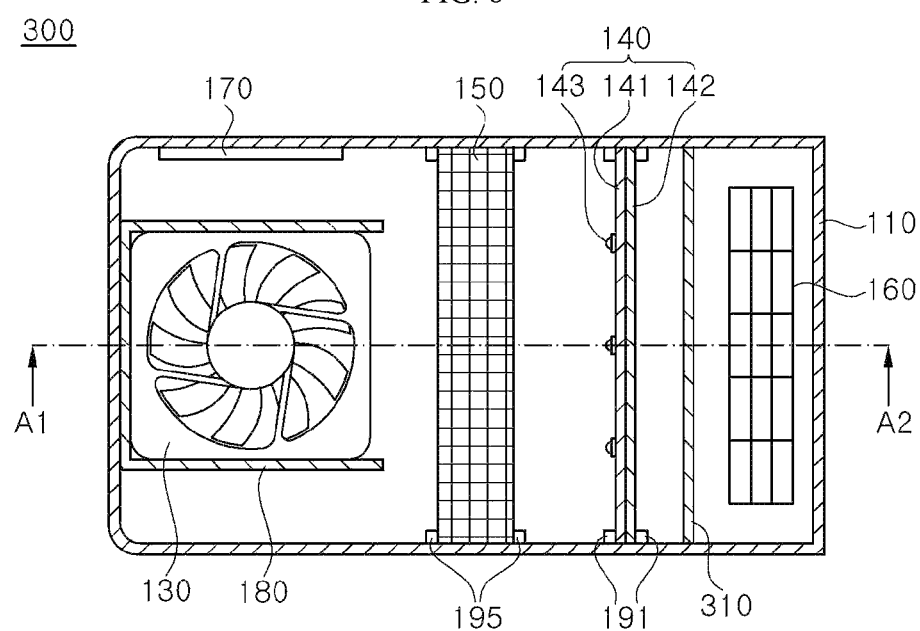
FIG. 8 is a top sectional view of a deodorization module according to a third exemplary embodiment of the inventive concepts.
Figure 9:
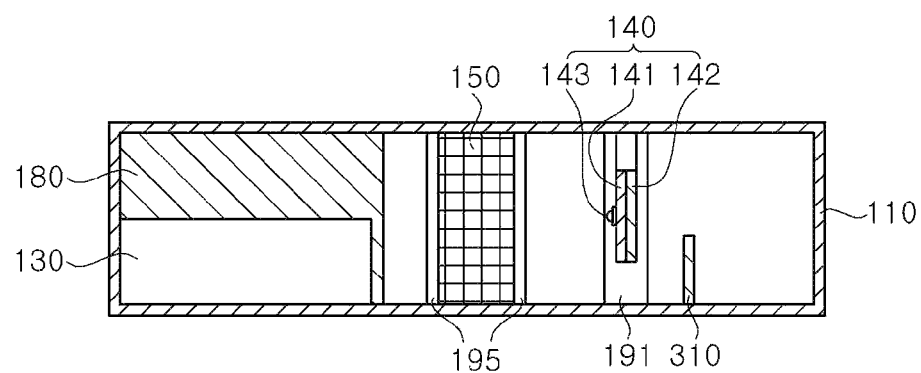
FIG. 9 is a side sectional view of the deodorization module according to the third exemplary embodiment.

FIG. 8 and FIG. 9 are views of a deodorization module according to a third exemplary embodiment of the inventive concepts.

FIG. 8 is a top sectional view of a deodorization module according to a third exemplary embodiment of the inventive concepts. FIG. 9 is a side sectional view of the deodorization module according to the third exemplary embodiment.

With regard to the deodorization module 300 according to the third exemplary embodiment, detailed description of the same components as those of the deodorization module 100 according to the first exemplary embodiment and the deodorization module 200 according to the second exemplary embodiment will be omitted. For omitted details, refer to the description with reference to FIG. 1 to FIG. 7.

In this exemplary embodiment, the photocatalyst bar 150 is disposed between the fan 130 and the light source module 140. In addition, the light source module 140 is disposed between the photocatalyst bar 150 and the discharge hole 160.

In this exemplary embodiment, a bottom discharge guide 310 is formed on the bottom of the housing 110. The bottom discharge guide 310 is formed between the light source module 140 and the discharge hole 160 to have a predetermined height.

Air passing through the photocatalyst bar 150 travels along the shortest path to the discharge hole 160. Thus, most of the air passes through a lower portion of the photocatalyst bar 150. According to the inventive concepts, the bottom discharge guide 310 formed between the photocatalyst bar 150 and the discharge hole 160 prevents a flow of the air from being concentrated in a certain area. That is, with the bottom discharge guide 310, the air can pass throughout the entire one surface of the photocatalyst bar 150.

Figure 10:
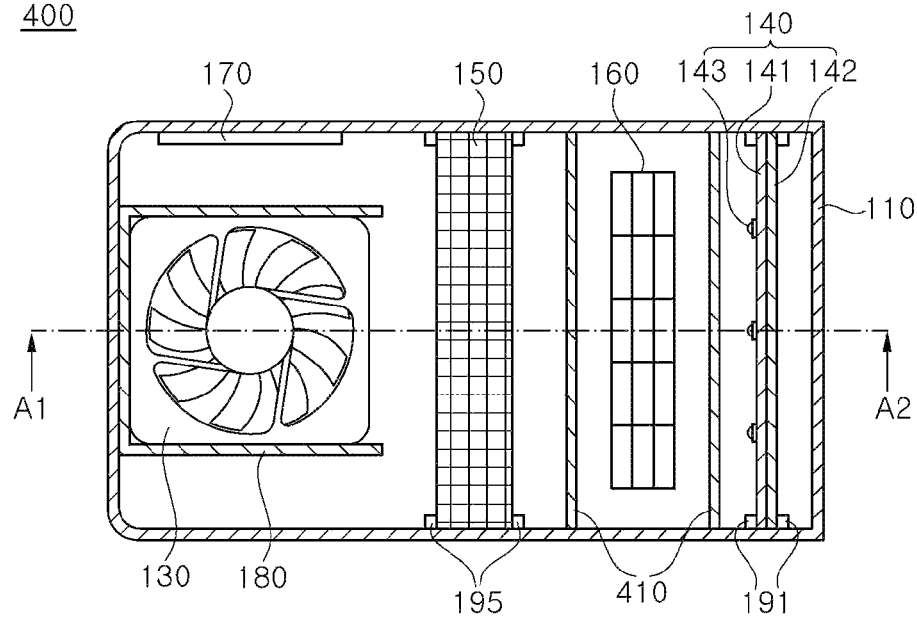
FIG. 10 is a top sectional view of a deodorization module according to a fourth exemplary embodiment of the inventive concepts.
Figure 11:
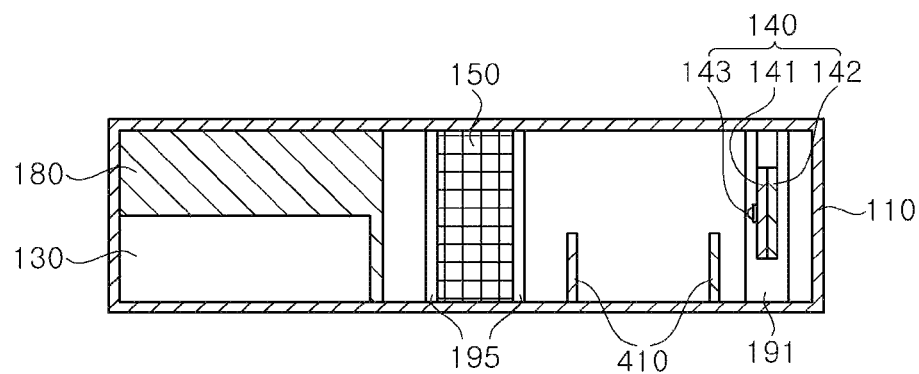
FIG. 11 is a side sectional view of the deodorization module according to the fourth exemplary embodiment.
Figure 12:
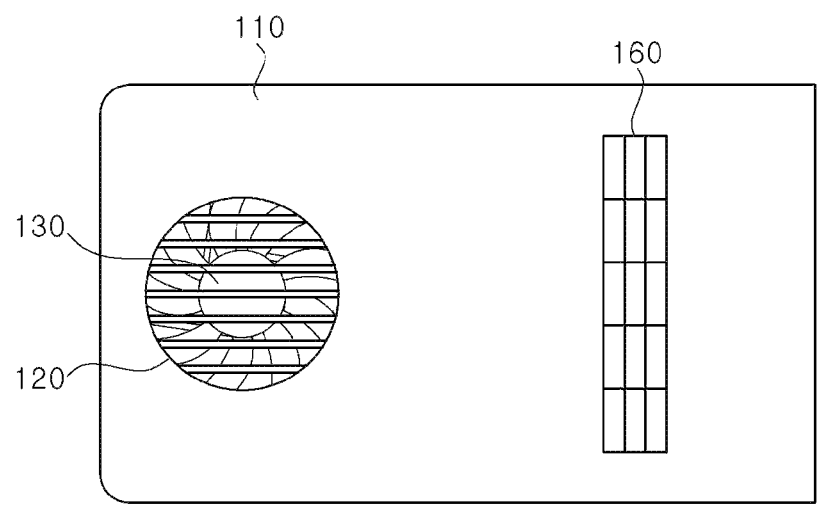
FIG. 12 is a bottom elevation view of the deodorization module according to the fourth exemplary embodiment.

FIG. 10 to FIG. 12 are views of a deodorization module according to a fourth exemplary embodiment of the inventive concepts.

FIG. 10 is a top sectional view of a deodorization module according to a fourth exemplary embodiment of the inventive concepts. FIG. 11 is a side sectional view of the deodorization module according to the fourth exemplary embodiment. FIG. 12 is a bottom elevation view of the deodorization module according to the fourth exemplary embodiment.

With regard to the deodorization module 400 according to the fourth exemplary embodiment, detailed description of the same components as those of the deodorization modules 100 to 300 according to the first to third exemplary embodiments will be omitted. For omitted details, refer to the description with reference to FIG. 1 to FIG. 9.

In this exemplary embodiment, the photocatalyst bar 150 is disposed between the fan 130 and the discharge hole 160.

In addition, the light source module 140 is disposed between the discharge hole 160 and the rear inner surface of the housing 110. Here, the light source module 140 is spaced apart from the rear inner surface of the housing 110. Accordingly, it is possible to prevent heat generated by the light source module 140 from being directly transferred to the housing 110. Further, it is possible to prevent condensation on the housing 110 due to heat generated by the light source module 140.

In this exemplary embodiment, the discharge hole 160 may be formed through the bottom of the housing 110 between the photocatalyst bar 150 and the light source module 140.

The housing 110 includes a pair of bottom discharge guides 410 protruding upward from the bottom of the housing 110. The pair of bottom discharge guides 410 is formed between the photocatalyst bar 150 and the discharge hole 160 and between the discharge hole 160 and the light source module 140, respectively. Although it has been described that the pair of bottom discharge guides 410 is formed at opposite sides of the discharge hole 160, respectively, it should be understood that the inventive concepts are not limited thereto. For example, the bottom discharge guide 410 between the discharge hole 160 and the light source module 140 may be omitted.

FIG. 13 to FIG. 16 are views of a deodorization module according to a fifth exemplary embodiment of the inventive concepts.

Figure 13:
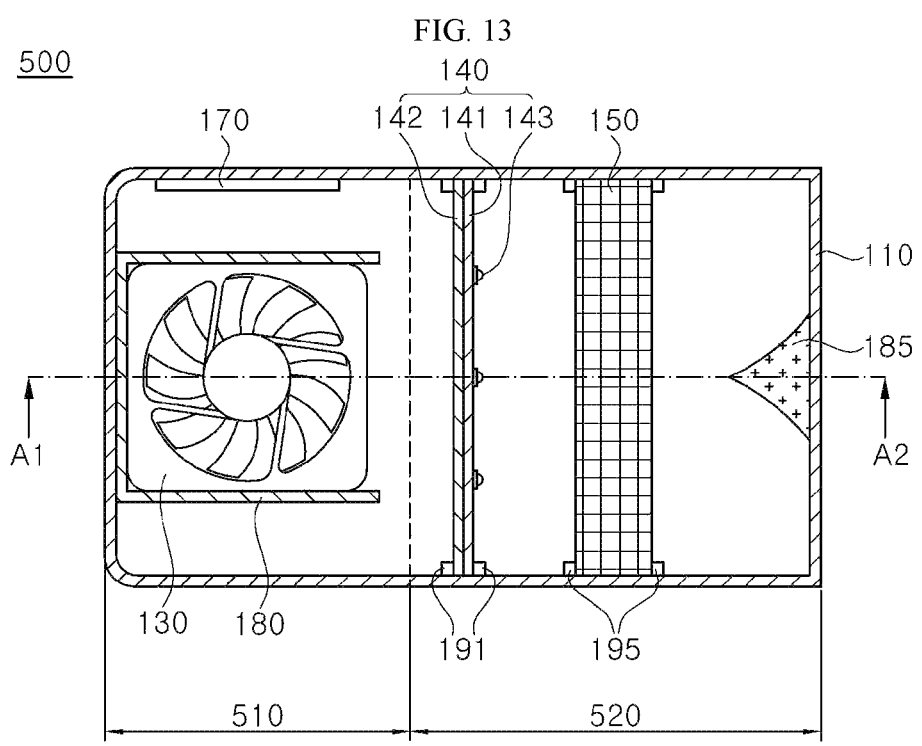
FIG. 13 is a top sectional view of a deodorization module according to a fifth exemplary embodiment of the inventive concepts.
Figure 14:
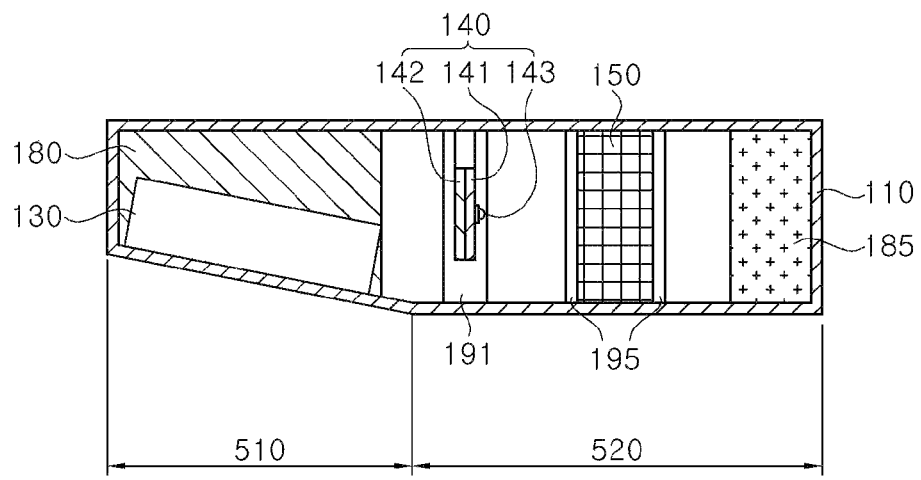
FIG. 14 is a side sectional view of the deodorization module according to the fifth exemplary embodiment.
Figure 15:
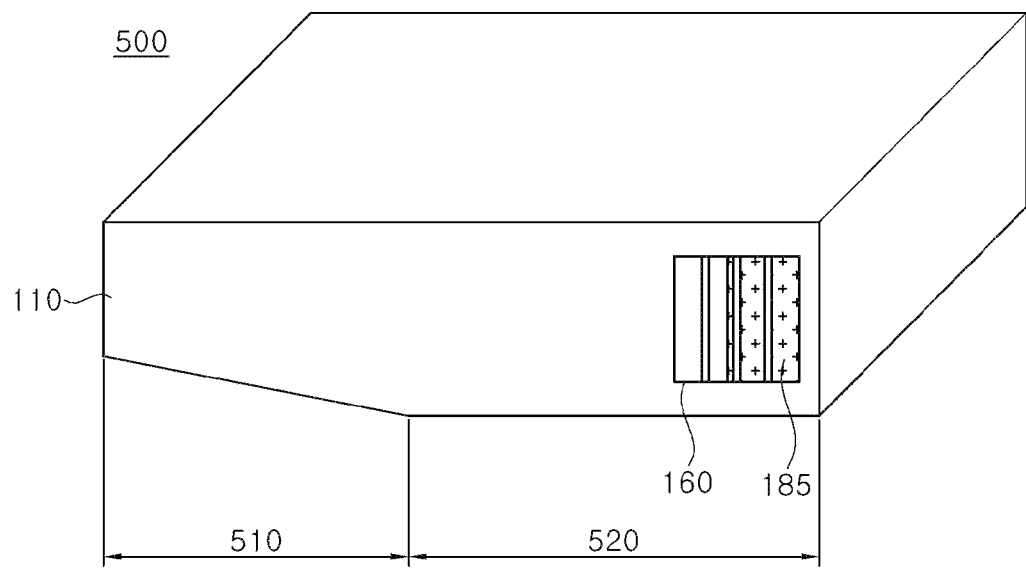
FIG. 15 is a side view of the deodorization module according to the fifth exemplary embodiment.
Figure 16:
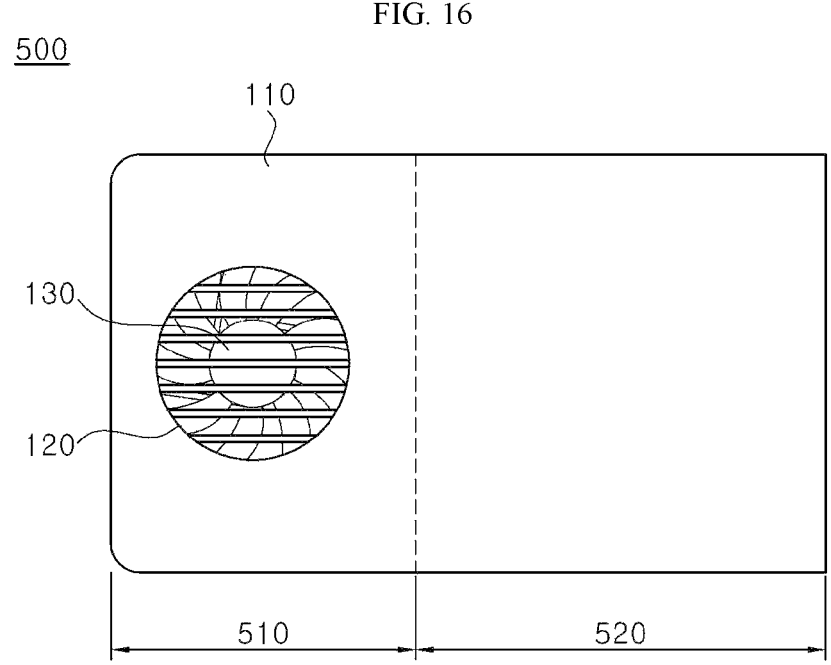
FIG. 16 is a bottom elevation view of the deodorization module according to the fifth exemplary embodiment.

FIG. 13 is a top sectional view of a deodorization module according to a fifth exemplary embodiment of the inventive concepts. FIG. 14 is a side sectional view of the deodorization module according to the fifth exemplary embodiment. FIG. 15 is a side view of the deodorization module according to the fifth exemplary embodiment. FIG. 16 is a bottom elevation view of the deodorization module according to the fifth exemplary embodiment.

With regard to the deodorization module 500 according to the fifth exemplary embodiment, detailed description of the same components as those of the deodorization modules 100 according to the first exemplary embodiment will be omitted. For omitted details, refer to the description with reference to FIG. 1 to FIG. 4.

In this exemplary embodiment, the deodorization module 500 is divided into a suction section 510 and a deodorization section 520.

The suction section 510 is a region where air is sucked into the deodorization module 500. The deodorization section 520 is a region where the air sucked into the deodorization module 500 is deodorized. The air deodorized in the deodorization section 520 is discharged outside the deodorization module 500.

The suction section 510 is provided with the suction hole 120 and the fan 130. In addition, the deodorization section 520 is provided with the light source module 140, the photocatalyst bar 150, and the discharge hole 160.

In this exemplary embodiment, the suction section 510 may have an inclined surface. Specifically, the suction section 510 is gradually reduced in height toward the front side of the housing 110. Since the suction section 510 has such an inclined surface, the fan 130 in the suction section 510 is also disposed in the housing 110 in an inclined manner.

Figure 17:
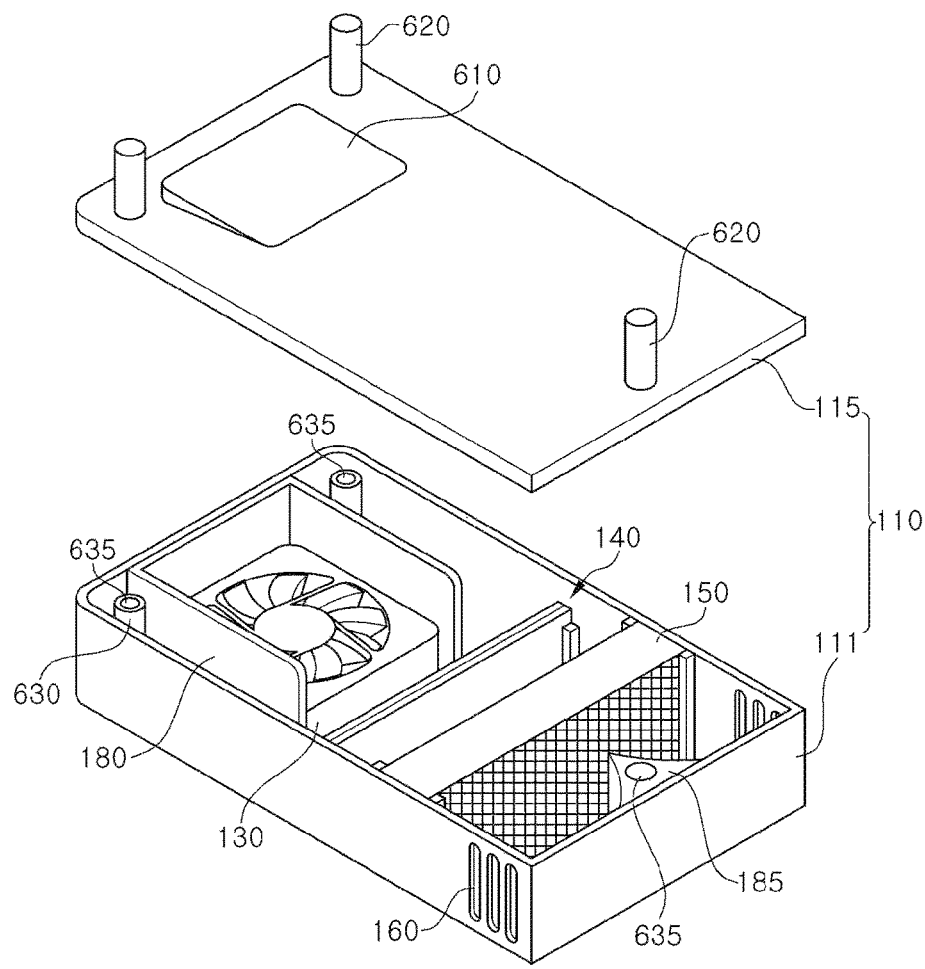
FIG. 17 is a side view of a deodorization module according to a sixth exemplary embodiment of the inventive concepts.

FIG. 17 is a view of a deodorization module according to a sixth exemplary embodiment of the inventive concepts.

Referring to FIG. 17, the housing 110 of the deodorization module 600 is divided into a main body 111 and a cover 115.

In this exemplary embodiment, the cover 115 is detachably coupled to the main body 111.

The main body 111 has an open top and accommodates the suction hole 120, the fan 130, the discharge hole 160, the photocatalyst bar 150, and the light source module 140. Components provided to the main body 111 are the same as those of any one of the deodorization modules according to the first to fifth exemplary embodiments. For details of the components provided to the main body 111, refer to the description with reference to FIG. 1 to FIG. 16.

The cover 115 covers the open top of the main body 111. For convenience of explanation, the cover 115 is shown as upside down in FIG. 17. In other words, a surface of the cover 115 on which a cover guide 610 is formed is a lower surface of the cover 115. That is, the cover 115 includes the cover guide 610 formed on the lower surface thereof. With the cover 115 coupled to the main body 111, the cover guide 610 is located above the fan 130. The cover guide 610 is gradually reduced in thickness toward a rear end thereof. With the cover guide 610 having such a shape, pressure loss of air sucked in by the fan 130 can be reduced.

In addition, the cover 115 includes a cover fastening member 620 formed on the lower surface thereof. The cover fastening member 620 protrudes downward from the lower surface of the cover 115.

The main body 111 includes a main body fastening member 630 formed thereon. The main body fastening member 630 corresponds in position to the cover fastening member 620. Referring to FIG. 17, the main body fastening member 630 protrudes upward from a lower inner surface of the main body 111. In addition, the main body fastening member 630 is formed with a fastening groove 635 corresponding in size to the cover fastening member 620. The fastening groove 635 may also be formed on the rear discharge guide 185.

The cover 115 is securely coupled to the main body 111 by inserting the cover fastening member 620 into the fastening groove 635 of the main body fastening member 630.

In this exemplary embodiment, it has been described that the main body is formed with the fastening groove 635 and the cover 115 is formed with the cover fastening member 620 protruding therefrom. However, it should be understood that a method of coupling the cover 115 to the main body 111 is not limited thereto. That is, coupling between the main body 111 and the cover 115 may be achieved by any suitable method known in the art.

In this exemplary embodiment, the cover 115 is described as one surface of the housing 110. However, a method of establishing a boundary between the main body 111 and the cover 115 is not limited thereto. That is, the boundary between the main body 111 and the cover 115 may be established in various ways, as needed.

Figure 18:
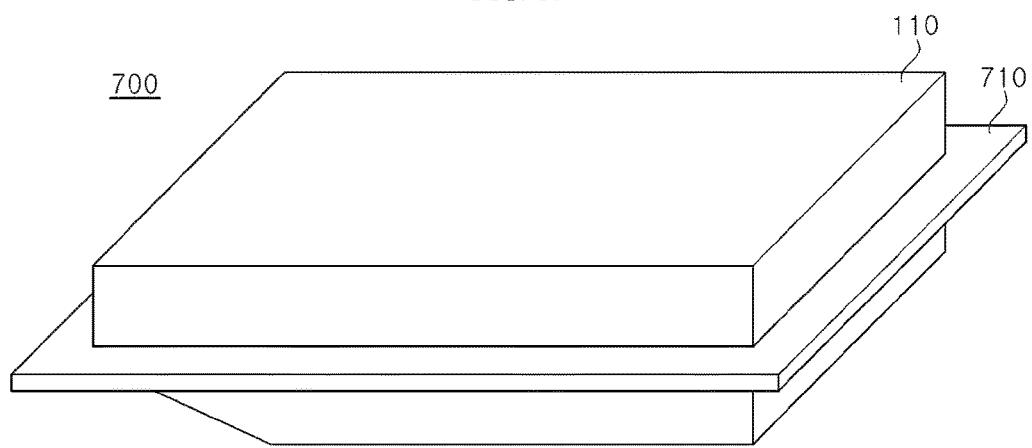
FIG. 18 is a bottom elevation view of the deodorization module according to the sixth exemplary embodiment.
Figure 19:
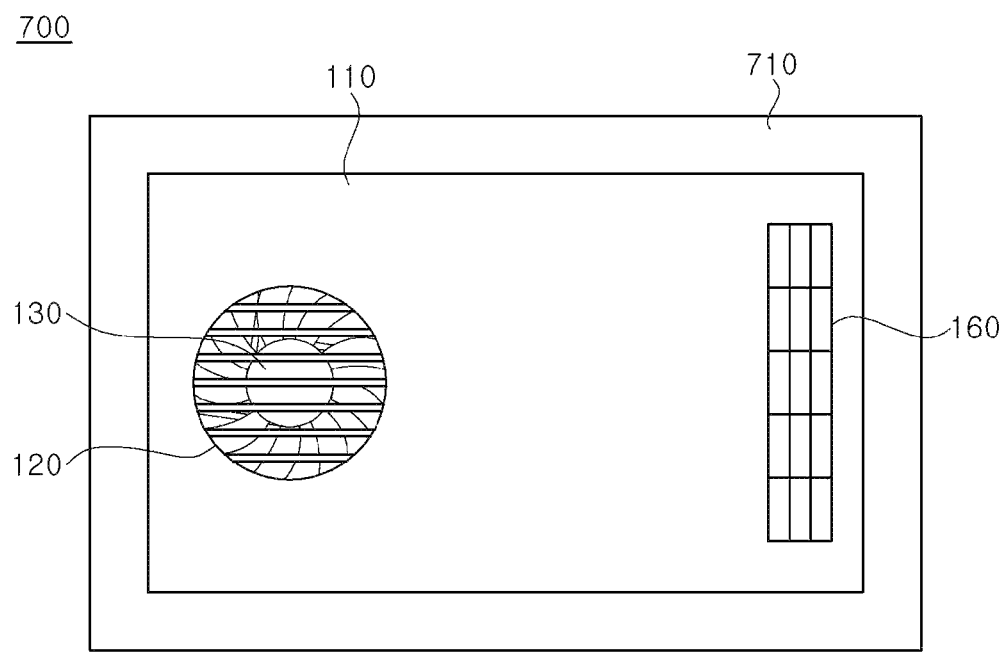
FIG. 19 is an exemplary view of a deodorization module according to a seventh exemplary embodiment of the inventive concepts.

FIG. 18 and FIG. 19 are views of a deodorization module according to a seventh exemplary embodiment of the inventive concepts.

FIG. 18 is a side view of the deodorization module according to the seventh exemplary embodiment. FIG. 19 is a bottom elevation view of the deodorization module according to the seventh exemplary embodiment.

FIG. 18 and FIG. 19 show an exterior of the housing 110 of the deodorization module 700 according to the seventh exemplary embodiment. The interior of the deodorization module 700 is the same as that of any one of the deodorization modules 100 to 600 according to the first to sixth exemplary embodiments of the disclosure.

In this exemplary embodiment, the housing 110 includes an external guide 710 formed on an outer surface thereof. The external guide 710 protrudes outward around the outer periphery of the housing 110. With the external guide 710, the depth to which the deodorization module 700 is inserted into a refrigerator can be adjusted when the deodorization module 700 is mounted on the refrigerator. The external guide 710 may be provided to any of the deodorization modules according to the first to sixth exemplary embodiments of the inventive concepts. Here, the external guide 710 needs to be located above the suction hole 120 and the discharge hole 160 of the deodorization module 700. For example, the discharge hole 160 may be formed through the bottom of the housing 110. In addition, the discharge hole 160 may be formed through both side walls of the housing 110 below the external guide 710.

Figure 20:
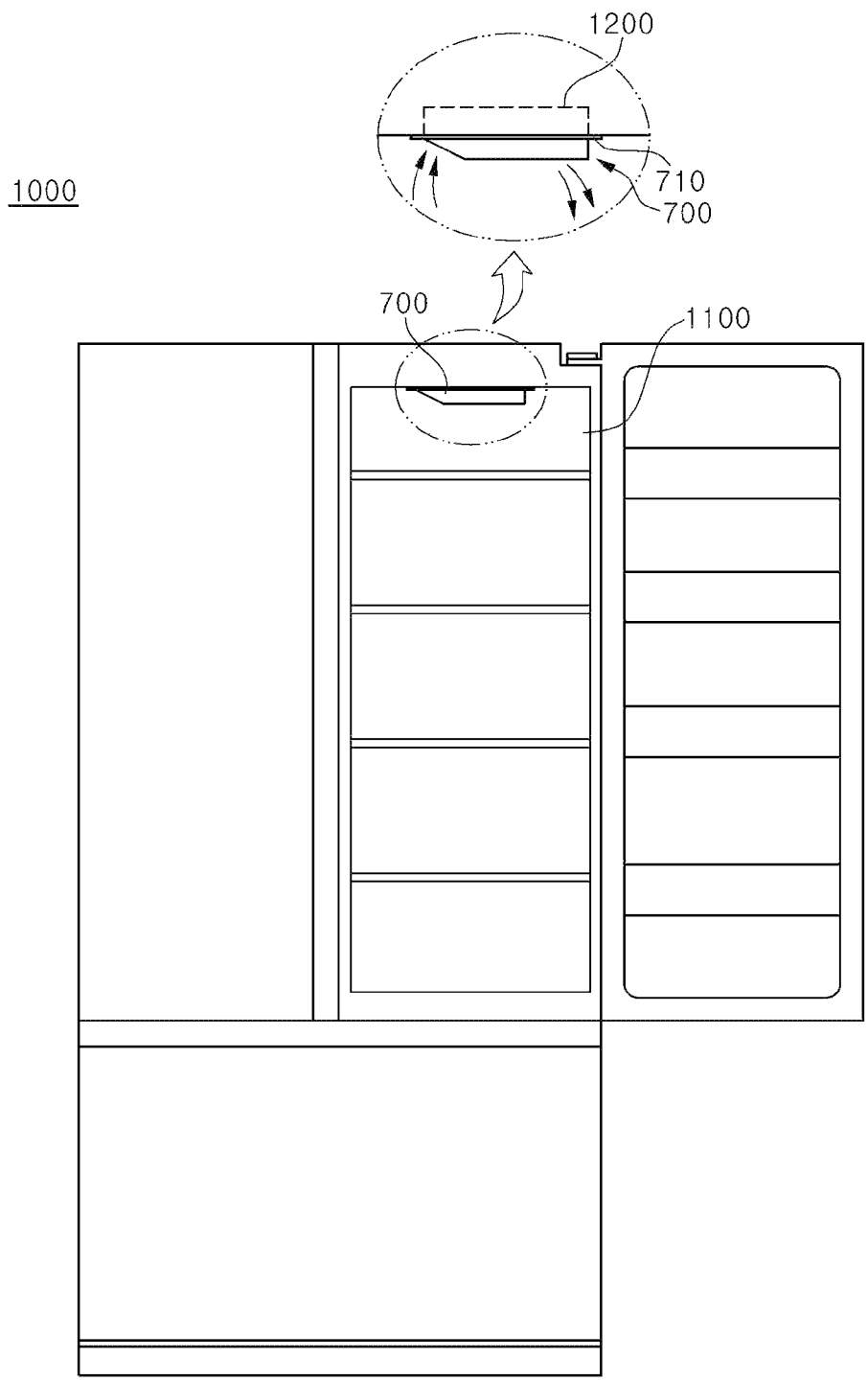
FIG. 20 is an exemplary view of a storage apparatus according to a first exemplary embodiment of the inventive concepts.

FIG. 20 is an exemplary view of a storage apparatus according to a first exemplary embodiment of the inventive concepts.

Referring to FIG. 20, the storage apparatus 1000 according to the first exemplary embodiment includes a storage chamber 1100 and a deodorization module 700.

In this exemplary embodiment, the storage apparatus 1000 is a refrigerator.

The storage chamber 1100 has an internal space. Food is stored in the interior space of the storage chamber 1100.

In addition, the storage chamber 1100 is formed with a deodorization module mount 1200 into which the deodorization module 700 is inserted. The deodorization module mount 1200 is provided in the form of a groove on an inner wall of the storage chamber 1100. Further, the deodorization module mount 1200 corresponds in shape to a portion of the deodorization module 700 which is inserted into the deodorization module mount.

The deodorization module 700 is the deodorization module according to the seventh exemplary embodiment. The deodorization module 700 is mounted on the deodorization module mount 1200. Here, an upper portion of the deodorization module 700 with respect to the external guide 710 is inserted into the deodorization module mount 1200, while a lower portion of the deodorization module 700 is located in the internal space of the storage chamber 1100. Accordingly, the suction hole and the discharge hole formed through the bottom of the deodorization module 700 are exposed to the internal space of the storage chamber 1100.

In this exemplary embodiment, the bottom of the deodorization module 700 has an inclined portion. With the deodorization module 700 formed in this manner, available space of the storage chamber 1100 can be widened.

When the deodorization module 700 is inserted into the deodorization module mount 1200, an upper surface of the external guide 710 contacts an upper side of the storage chamber 1100. Here, the deodorization module 700 may be secured to the storage chamber 1100 by securing the external guide 710 to the upper side of the storage chamber 1100. For example, the external guide 710 may be secured to the upper side of the storage chamber 1100 using a screw or an adhesive.

Although the deodorization module 700 is shown as mounted on the upper side of the storage chamber 1100 in FIG. 20, it should be understood that the position of the deodorization module 700 is not limited thereto. That is, the deodorization module 700 may be disposed at any location on the storage chamber 1100.

In addition, although the deodorization module 700 is shown as inserted into the deodorization module mount to be mounted on the storage chamber 1100, it should be understood that the inventive concepts are not limited thereto. That is, the deodorization module mount 1200 may be omitted and the deodorization module 700 may be attached to the inner wall of the storage chamber 1100.

In this exemplary embodiment, the deodorization module is described as the deodorization module 700 according to the seventh exemplary embodiment. However, it should be understood that the inventive concepts are not limited thereto. That is, the deodorization module mounted on the storage apparatus 1000 may be any one of the deodorization modules according to the first to seventh exemplary embodiments.

The storage apparatus 1000 may further include a temperature control unit. The temperature control unit controls the temperature of the storage chamber 1100. For example, the temperature control unit controls the internal temperature of the storage chamber 1100 to be maintained within a range of 0° C. to 10° C.

In this exemplary embodiment, the storage apparatus 1000 is described as a refrigerator. However, it should be understood that the inventive concepts are not limited thereto and the storage apparatus 1000 may be any apparatus storing food. For example, the storage apparatus 1000 may be a heating cabinet.

Figure 21:
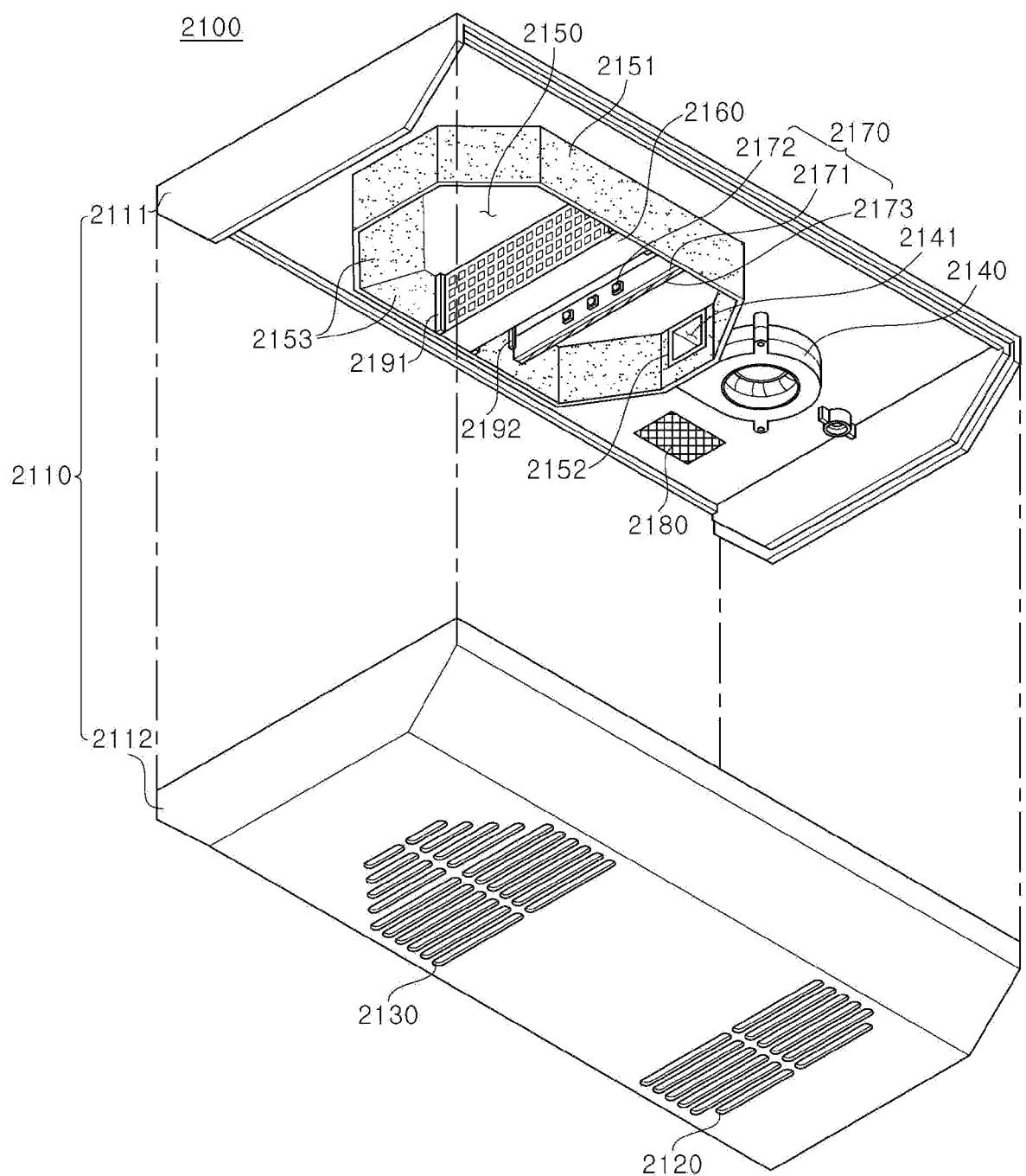
FIG. 21 is a perspective view of a deodorization module according to an eighth exemplary embodiment of the inventive concepts.
Figure 22:
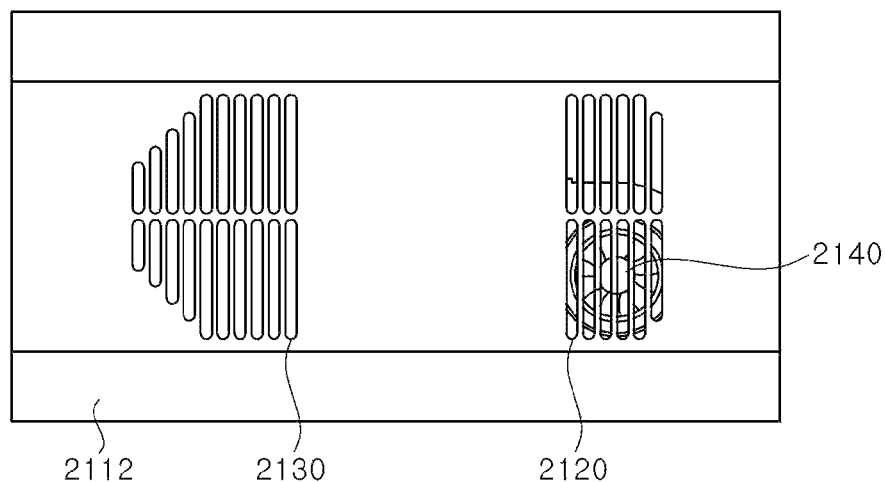
FIG. 22 is a bottom elevation view of the deodorization module according to the eighth exemplary embodiment.

FIG. 21 and FIG. 22 are exemplary views of a deodorization module according to an eighth exemplary embodiment of the inventive concepts.

FIG. 21 is a perspective view of a deodorization module according to an eighth exemplary embodiment of the inventive concepts. FIG. 22 is a bottom elevation view of the deodorization module according to the eighth exemplary embodiment.

In this exemplary embodiment, the deodorization module 2100 includes a housing 2110, a suction hole 2120, a fan 2140, a discharge hole 2130, a flow path 2150, a photocatalyst bar 2160, a light source module 2170, and a control board 2180.

The housing 2110 is configured to receive the fan 2140, the photocatalyst bar 2160, the light source module 2170, and the control board 2180. In addition, the housing 2110 is formed with the suction hole 2120 and the discharge hole 2130. The housing 2110 is formed therein with a flow path 2150 defined by a flow path side wall 2151.

The housing 2110 is divided into a main body 2111 and a cover 2112. The main body 2111 is open on at least one side thereof and receives the fan 2140, the flow path 2150, the photocatalyst bar 2160, and the light source module 2170. In addition, the cover 2112 has the suction hole 2120 and the discharge hole 2130 formed through one side thereof and covers the open side of the main body 2111.

In FIG. 21, the cover 2112 constitutes one surface and side surfaces of the housing 2110 and the main body 2111 constitutes the other surface of the housing 2110. However, it should be understood that the structure of the housing 2110 is not limited to thereto. That is, the housing 2110 may have any suitable structure, without limitation.

The fan 2140, the flow path 2150, the photocatalyst bar 2160, and the light source module 2170 are disposed on an inner wall of the main body 2111. Here, the inner wall of the main body 2111 faces the one surface of the cover 2112.

The cover 2112 is coupled to the main body 2111 to cover the fan 2140, the flow path 2150, the photocatalyst bar 2160, and the light source module 2170. Further, the distance between opposite side surfaces of the cover 2112 may be gradually reduced from one side to the other side of the cover 2112. When the opposite side surfaces of the cover 2112 are inclined toward one another, the deodorization module 2100 can have a smaller volume than when the opposite side surfaces of the cover 2112 are parallel to one another. Thus, the space occupied by the deodorization module 2100 can be reduced. However, it should be understood that the structures of the main body 2111 and the cover 2112 are not limited thereto. That is, the main body 2111 and the cover 2112 may have any suitable structures, without limitation. Here, the cover 2112 is detachably coupled to the main body 2111.

The housing 2110 may be formed of a reflective material, or the inner wall of the housing may be coated with a reflective material. Alternatively, the inner wall of the housing 2110 may be coated with a reflective material only at a portion corresponding to the flow path 2150.

The suction hole 2120 is a hole through which air outside the deodorization module 2100 is sucked into the housing 2110. The suction hole 2120 is formed through the one surface of the housing 2110. In addition, the suction hole 2120 is formed in a region where the fan 2140 is disposed.

The fan 2140 can easily redirect the air sucked in thereby. In this exemplary embodiment, the fan 2140 discharges the sucked air to the flow path 2150 located at one side of the fan 2140.

The fan 2140 is positioned between the suction hole 2120 and the other surface of the housing 2110. Here, the rotation axis of the fan 2140 is perpendicular to the suction hole 2120. Thus, the fan 2140 directly sucks in air outside the deodorization module 2100 through the suction hole 2120. In addition, the fan 2140 discharges the sucked air through a separate air outlet 2141. The fan 2140 may adjoin the suction hole 2120 or may be spaced apart from the suction hole. For example, the fan 2140 may be a centrifugal flow fan.

The fan 2140 may be secured to the inner wall of the housing 2110 using a screw. However, it should be understood that a method of securing the fan 2140 to the housing 2110 is not limited thereto. That is, the fan 2140 may be secured to the housing 2110 by any suitable method known in the art.

The discharge hole 2130 is a hole through which air deodorized inside the housing 2110 is discharged to the outside. The discharge hole 2130 is formed through the one surface of the housing 2110. Here, the discharge hole 2130 is located in a region where the flow path 2150 is formed. Specifically, the discharge hole 2130 is located in a region of the flow path 2150 at the side of an exit surface of the photocatalyst bar 2160. Here, the exit surface of the photocatalyst bar 2160 is a surface through which air exits the photocatalyst bar 2160.

The flow path 2150 is a path between the fan 2140 and the discharge hole 2130. The flow path 2150 is defined by the flow path side wall 2151 surrounding the photocatalyst bar 2160 and the light source module 2170.

A flow path opening 2152 is formed through the flow path side wall 2151 defining the flow path 2150. The flow path opening 2152 is connected to the air outlet 2141 of the fan 2140. The flow path opening 2152 has the same size as the air outlet 2141 of the fan 2140. Air sucked in by the fan 2140 is discharged to the flow path 2150 through the flow path opening 2152. One surface of the flow path side wall 2151 tightly contacts one inner surface of the housing 2110. In addition, the other surface of the flow path side wall 2151 tightly contacts the other inner surface of the housing 2110. Accordingly, the air introduced into the flow path 2150 is discharged from the housing 2110 through the discharge hole 2130. Here, the one inner surface of the housing 2110 is an inner wall of the cover 2112. In addition, the other inner surface of the housing 2110 is the inner wall of the main body 2111. Further, the one inner surface of the housing 2110 faces the other inner surface of the housing 2110.

In this exemplary embodiment, the flow path 2150 is gradually increased in width from the fan 2140 to a deodorization section. In addition, the flow path 2150 is gradually decreased in width from the deodorization section to a region in which the discharge hole 2130 is disposed. Here, the deodorization section is a section in which air deodorization is performed and the light source module 2170 and the photocatalyst bar 2160 are disposed. The deodorization section is the widest of all sections of the flow path 2150. That is, a section in which the photocatalyst bar 2160 and the light source module 2170 are disposed is the widest of all sections of the flow path 2150. For example, the flow path 2150 may have an octagonal cross section.

With the flow path 2150 having this structure, the air discharged from the fan 2140 can pass through the light source module 2170 and the photocatalyst bar 2160 while spreading widely. That is, deodorization of the air is performed in a wide space. As a result, air deodorization performance of the deodorization module can be improved.

A portion of the flow path side wall 2151 located between the inner wall of the housing 2110 and the light source module 2170 has an inclined inner surface 2153. That is, the portion of the flow path side wall 2151 is gradually reduced in thickness from the other surface to the one surface of the flow path side wall. The portion of the flow path side wall 2151 shaped in this manner serves to guide air inside the flow path 2150 to the discharge hole 2130. When moving to the discharge hole 2130, the air in the flow path 2150 collides against the flow path sidewall 2151, causing air pressure loss. The flow path side wall 2151 having the inclined inner surface 2153 exhibits lower air pressure loss than a flow path side wall without any inclined inner surface. That is, with the flow path sidewall 2151 according to this exemplary embodiment, air pressure loss can be reduced.

The flow path side wall 2151 may be formed of a reflective material or an inner surface of the flow path side wall may be coated with a reflective material.

The photocatalyst bar 2160 is disposed between the light source module 2170 and the discharge hole 2130 in the flow path 2150. The photocatalyst bar 2160 is provided in the form of a bar having a plurality of through-holes. For example, the photocatalyst bar 2160 may be formed of a porous ceramic material. Alternatively, the photocatalyst bar 2160 is formed of a metal foam including nickel (Ni), iron (Fe), aluminum (Al), chromium (Cr), and the like. A surface of the photocatalyst bar 2160 may be coated with a photocatalytic material. The photocatalytic material may include at least one selected from the group consisting of $TiO_2$, ZnO, $ZrO_2$, and $WO_3$. Alternatively, the photocatalyst bar 2160 itself may contain a photocatalytic material.

In this exemplary embodiment, UV light emitted from the UV light source 2172 reacts with the photocatalytic material of the photocatalyst bar 2160 to generate hydroxyl radicals (·OH). The hydroxyl radicals decompose and remove pollutants or odorous substances. That is, air introduced into the flow path 2159 is deodorized in the process of passing through the through-holes of the photocatalyst bar 2160.

Both side surfaces of the photocatalyst bar 2160 tightly contact the flow path side wall 2151. In addition, one surface of the photocatalyst bar 2160 tightly contacts the one inner surface of the housing 2110. Further, the other surface of the photocatalyst bar 2160 tightly contacts the other inner surface of the housing 2110. Thus, the air introduced into the flow path 2150 moves to the discharge hole 2130 through the photocatalyst bar 2160. That is, the air is necessarily deodorized by the photocatalyst bar 2160 and the light source module 2170 before being discharged from the housing 2110 through the discharge hole 2130.

The photocatalyst bar 2160 may be secured in the flow path 2150 using a pair of bar securing members 2191. The pair of bar securing members 2191 is formed on the flow path side wall 2151 and protrudes inward from the flow path side wall. In addition, each of the pair of bar securing members 2191 has a vertical groove formed thereon to extend from one end to the other end thereof. The photocatalyst bar 2160 is secured in the flow path 2150 by inserting opposite side surfaces of the photocatalyst bar 2160 into the grooves of the pair of bar securing members 2191, respectively.

In this exemplary embodiment, it has been described that the photocatalyst bar 2160 is secured in the flow path 2150 using the pair of bar securing members 2191. However, a method of securing the photocatalyst bar 2160 in the flow path 2150 is not limited thereto. In order to secure the photocatalyst bar 2160 in the flow path 2150, any known method may be employed by those skilled in the art.

The light source module 2170 is disposed between the fan 2140 and the photocatalyst bar 2160 in the flow path 2150. Both side surfaces of the light source module 2170 tightly contact the flow path side wall 2151. Here, the side surfaces of the light source module 2170 refer to side surfaces of a light source substrate 2171 and side surfaces of a heat sink 2173. However, when the heat sink 2173 is omitted or is formed at a portion of the light source substrate 2171, the side surfaces of the light source module 2170 may refer to the side surfaces of the light source substrate 2171.

One surface of the light source module 2170 is spaced apart from the one inner surface of the housing 2110. The other surface of the light source module 2170 is spaced apart from the other inner surface of the housing 2110. That is, spaces are created between the one surface of the light source module 2170 and the housing 2110 and between the other surface of the light source module 2170 and the housing 2110, respectively. Air introduced into the flow path 2150 moves through the spaces.

The light source module 2170 may be secured in the flow path 2150 using a pair of module securing members 2192. The pair of module securing members 2192 is formed on the flow path side wall 2151 and protrudes inward from the flow path side wall. In addition, each of the pair of module securing members 2192 has a vertical groove formed thereon to extend from one end thereof. The depth of the vertical groove may vary depending on the height at which the light source module 2170 is to be positioned. The light source module 2170 is secured in the flow path 2150 by inserting the opposite side surfaces of the light source module 2170 into the grooves of the pair of module securing members 2192, respectively.

In this exemplary embodiment, it has been described that the light source module 2170 is secured in the flow path 2150 using the pair of module securing members 2192. However, a method of securing the light source module 2170 in the flow path 2150 is not limited thereto. In order to secure the light source module 2170 in the flow path 2150, any known method may be employed by those skilled in the art.

The light source module 2170 includes a light source substrate 2171, a UV light source 2172, and a heat sink 2173.

The light source substrate 2171 is electrically connected to the UV light source 2172 and applies an electrical signal to the UV light source 2172. For example, the light source substrate 2171 may be a printed circuit board or a metal printed circuit board. When the light source substrate 2171 is a metal printed circuit board, the deodorization module 2100 can have improved heat dissipation performance.

The UV light source 2172 is mounted on one surface of the light source substrate 2171 to emit UV light toward the photocatalyst bar 2160. The UV light source 2172 emits UV light toward an entrance surface of the photocatalyst bar 2160. Here, the entrance surface of the photocatalyst bar 2160 refers to a surface of the photocatalyst bar 2160 through which air enters the photocatalyst bar 2160. For example, the UV light source 2172 may be an LED chip. The UV light source 2172 may include one or more UV light sources. When multiple UV light sources 2172 are mounted on the light source substrate 2171, UV light can be evenly radiated throughout the entrance surface of the photocatalyst bar 2160. The number of UV light sources 143 may be adjusted, as needed.

The heat sink 2173 is configured to dissipate heat from the UV light source 2172 and the light source substrate 2171. The heat sink 2173 is disposed on the other surface of the light source substrate 2171. The heat sink 2173 may be attached to the other surface of the light source substrate 2171 using a thermally conductive adhesive. The heat sink 142 is formed of a thermally conductive material. For example, the heat sink 2173 may be formed of a metal. In this exemplary embodiment, it has been described that the light source module 2170 includes the heat sink 2173. However, it should be understood that the inventive concepts are not limited thereto. The heat sink 2173 may be omitted, as needed. In addition, the heat sink 2173 may have any suitable structure known in the art and may be formed by any suitable method known in the art.

The control board 2180 supplies electrical power and control signals to the fan 2140 and the light source module 2170. The control board 2180 is electrically connected to each of the fan 2140 and the light source module 2170 via a cable. In this exemplary embodiment, it has been described that the fan 2140 and the light source module 2170 receive electrical power and control signals from a single common control board 2180. However, it should be understood that the inventive concepts are not limited thereto and the fan 2140 and the light source module 2170 may receive electrical power and control signals from different control boards, respectively.

In FIG. 21, it has been described that the photocatalyst bar 2160 and the light source module 2170 are secured in the flow path 2150 using the pair of bar securing members 2191 and the pair of module securing members 2192, respectively. However, it should be understood that the inventive concepts are not limited thereto. That is, the pair of bar securing members 2191 and the pair of module securing members 2192 may be omitted, as needed. In this case, the photocatalyst bar 2160 and the light source module 2170 may be secured in the flow path 2150 by any other suitable method known in the art.

Figure 23:
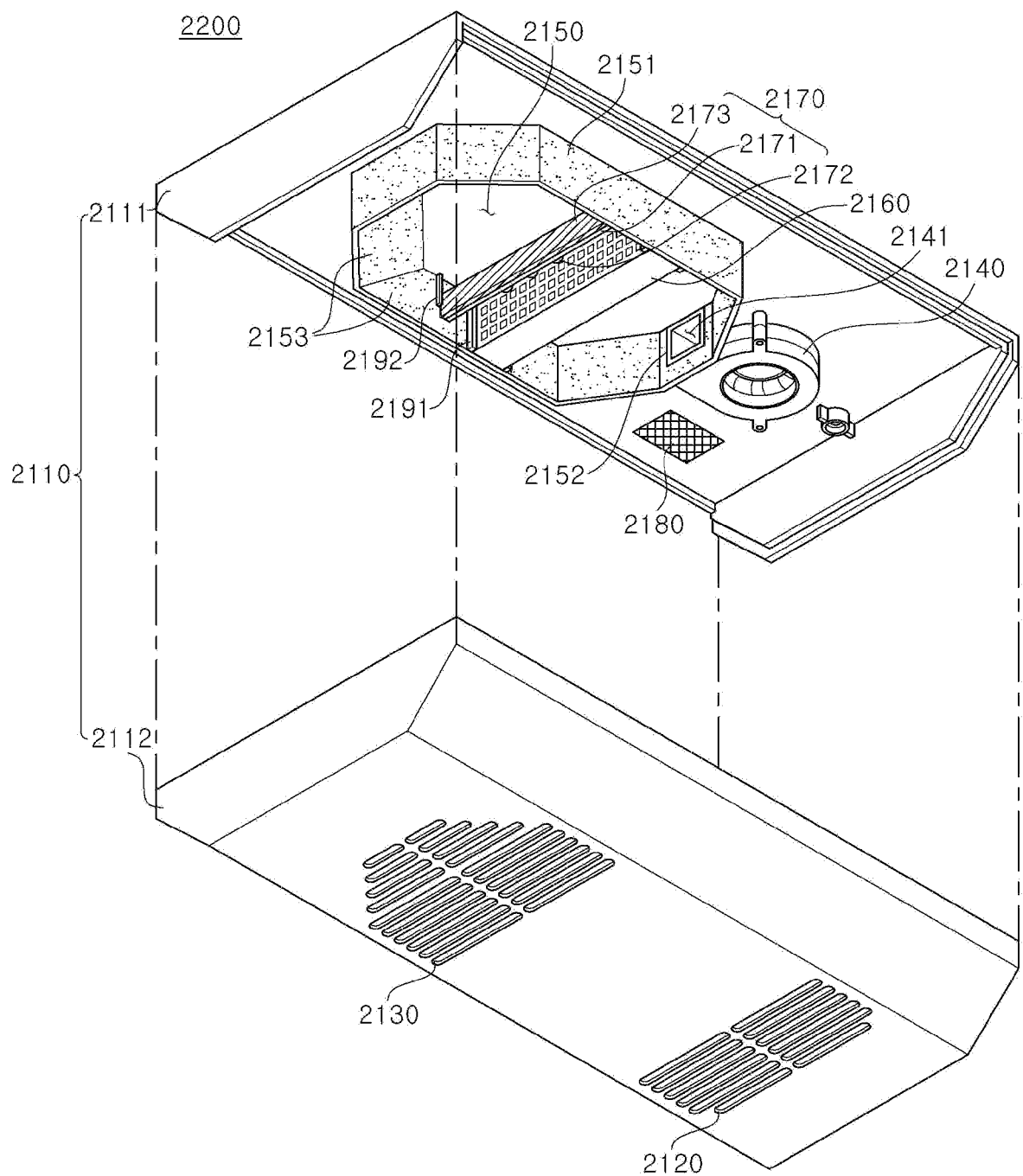
FIG. 23 is a perspective view of a deodorization module according to a ninth exemplary embodiment of the inventive concepts.

FIG. 23 is a perspective view of a deodorization module according to a ninth exemplary embodiment of the inventive concepts.

With regard to the deodorization module 2200 according to the ninth exemplary embodiment, detailed description of the same components as those of the deodorization module according to the eighth exemplary embodiment will be omitted. For omitted details with regard to FIG. 23, refer to the description with reference to FIG. 21 and FIG. 22.

In this exemplary embodiment, the photocatalyst bar 2160 and the light source module 2170 are disposed in the flow path 2150.

The photocatalyst bar 2160 is disposed between the fan 2140 and the light source module 2170.

In addition, the light source module 2170 is disposed between the photocatalyst bar 2160 and the discharge hole 2130. The UV light source 2172 of the light source module 2170 emits UV light toward the exit surface of the photocatalyst bar 2160.

Figure 24:
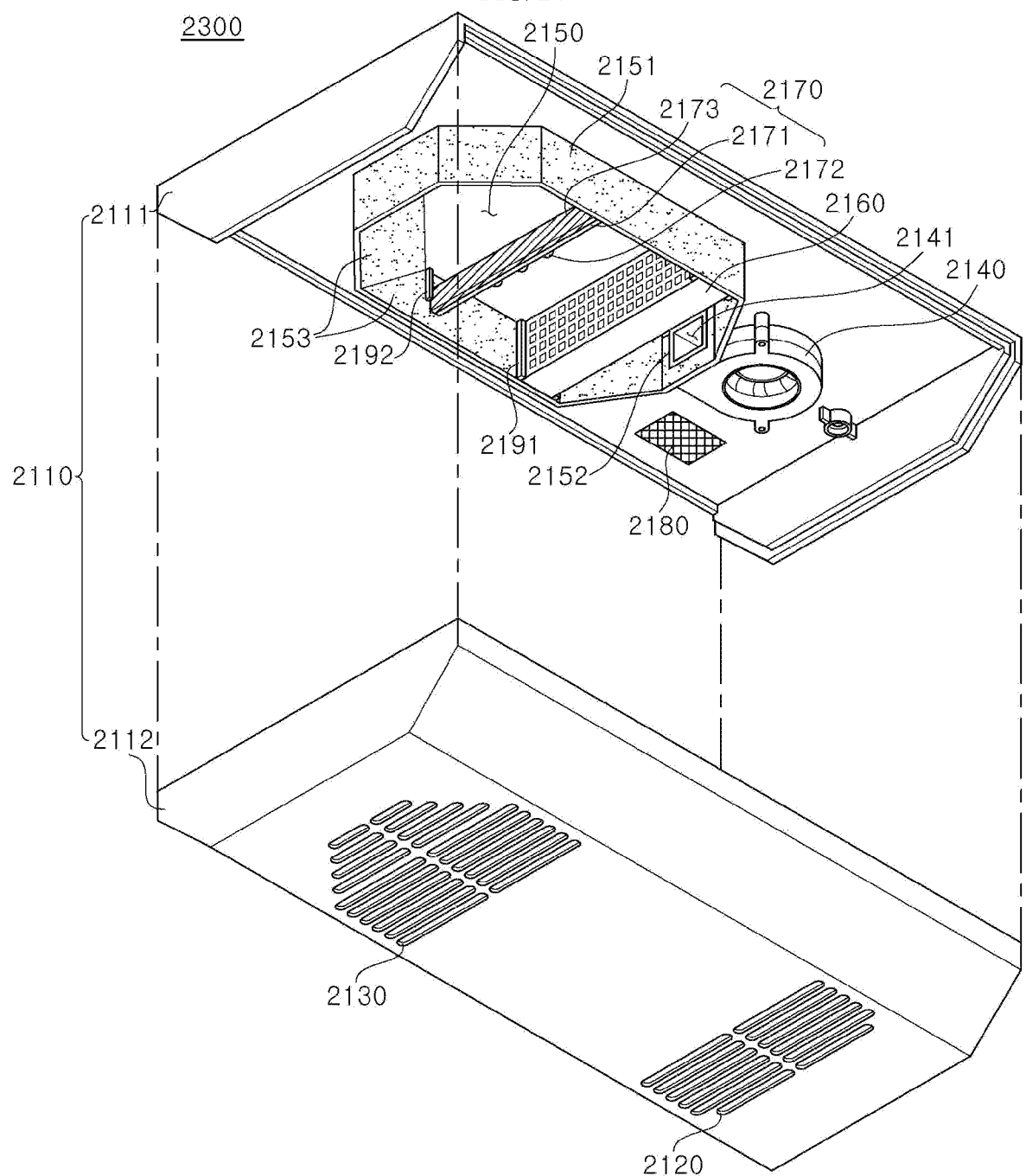
FIG. 24 is a perspective view of a deodorization module according to a tenth exemplary embodiment of the inventive concepts.

FIG. 24 is a perspective view of a deodorization module according to a tenth exemplary embodiment of the inventive concepts.

With regard to the deodorization module 2300 according to the tenth exemplary embodiment, detailed description of the same components as those of the deodorization module according to the eighth exemplary embodiment will be omitted. For omitted details with regard to FIG. 24, refer to the description with reference to FIG. 21 and FIG. 22.

In this exemplary embodiment, the photocatalyst bar 2160 and the light source module 2170 are disposed in the flow path 2150.

The photocatalyst bar 2160 is disposed between the fan 2140 and the light source module 2170.

In addition, the light source module 2170 is disposed between the photocatalyst bar 2160 and a portion of flow path side wall 2151. Here, the portion of flow path side wall 2151 refers to a portion which faces the exit surface of the photocatalyst bar 2160.

Figure 25:
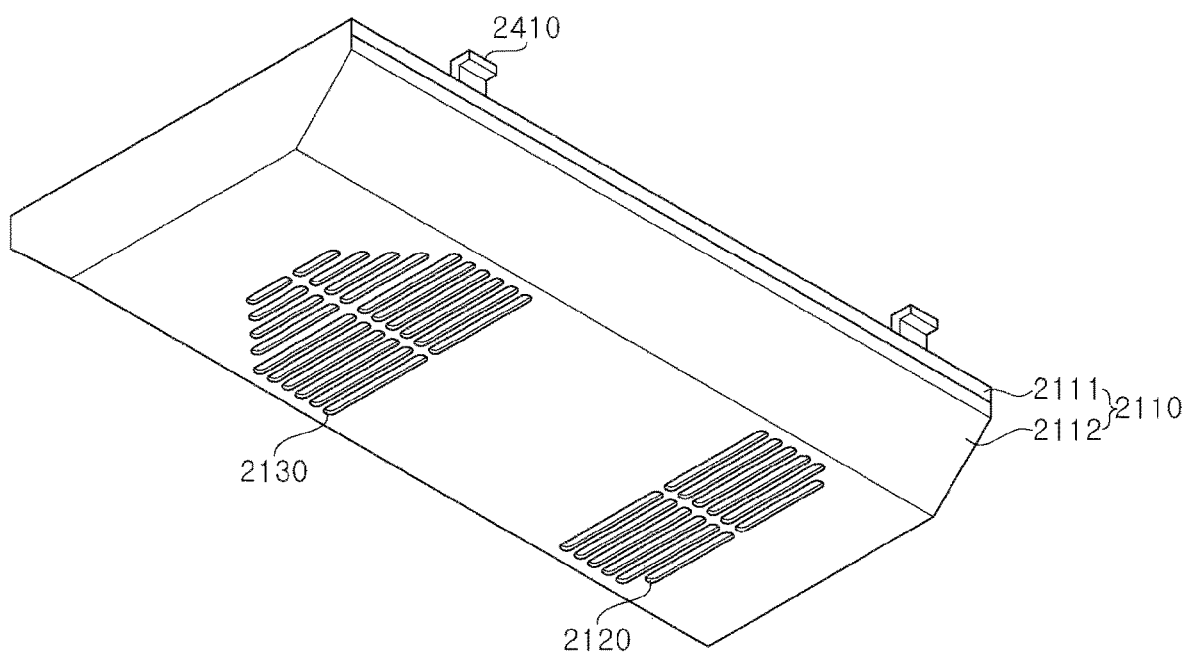
FIG. 25 is an exemplary view of a deodorization module according to an eleventh exemplary embodiment of the inventive concepts.

FIG. 25 is an exemplary view of a deodorization module according to an eleventh exemplary embodiment of the inventive concepts.

An internal structure of the deodorization module 2400 according to the eleventh exemplary embodiment is the same as that of any one of the deodorization modules according to the eighth to tenth exemplary embodiments of the disclosure. For details of the internal structure of the deodorization module 2400 according to the eleventh exemplary embodiment, refer to the description with regard to the deodorization modules according to eighth to tenth exemplary embodiments of the disclosure.

In this exemplary embodiment, the housing 2110 includes a fastening member 2410. The fastening member 2410 protrudes outward from an outer wall of the housing 2110. In addition, the fastening member 2410 has a bent portion. Further, the fastening member 2410 has elasticity. That is, the fastening member 2410 is deformed upon application of force exceeding a predetermined level and returns to the original form thereof upon removal of the force. For example, the fastening member 2410 may be formed of a plastic material. Alternatively, the fastening member 2410 may be formed of a thin metal.

The deodorization module 2400 may be mounted on a storage apparatus such as a refrigerator using the fastening member 2410.

Figure 26:
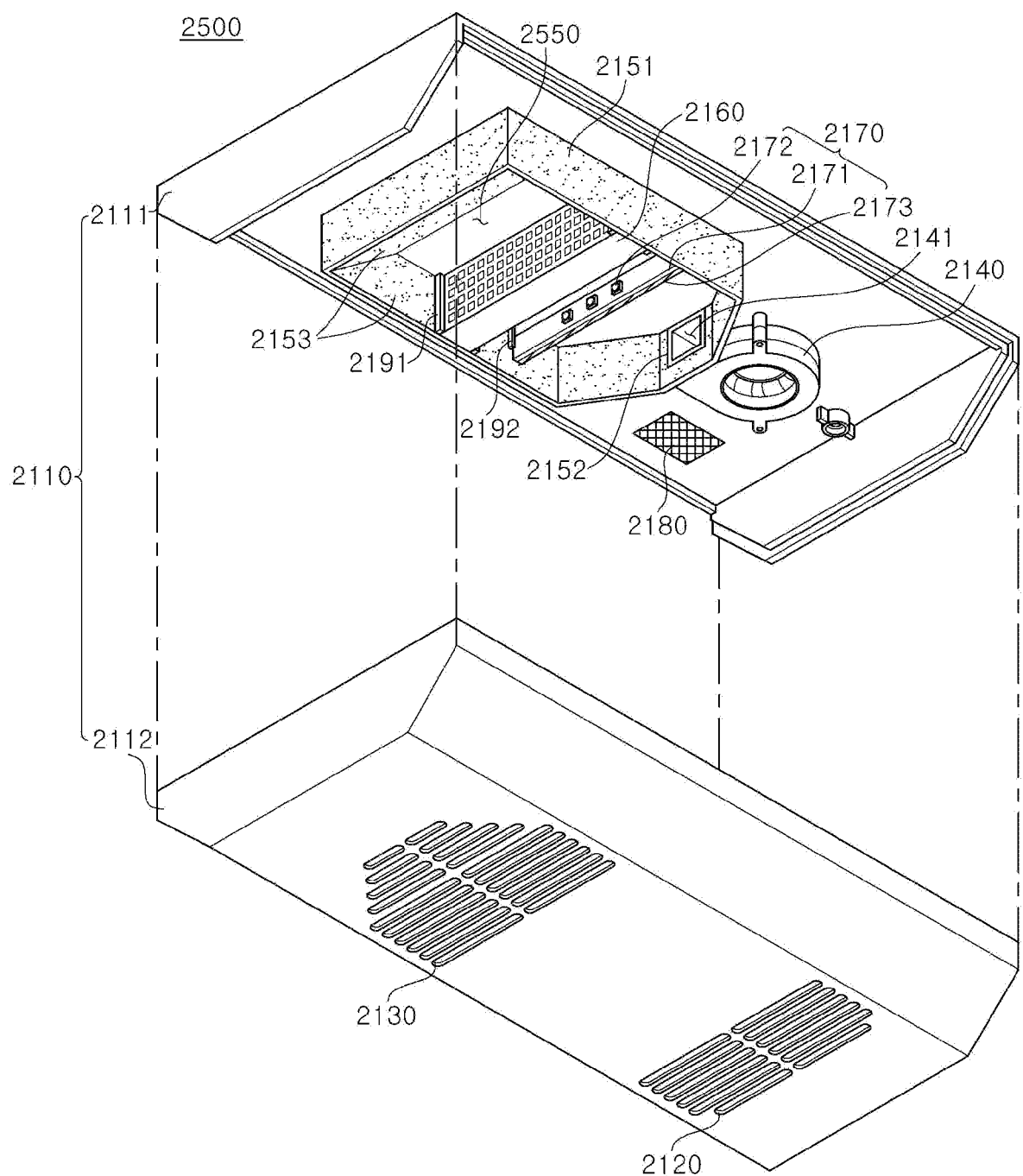
FIG. 26, FIG. 27, and FIG. 28 are exemplary views of respective flow paths for a deodorization module according to exemplary embodiments of the inventive concepts.
Figure 27:
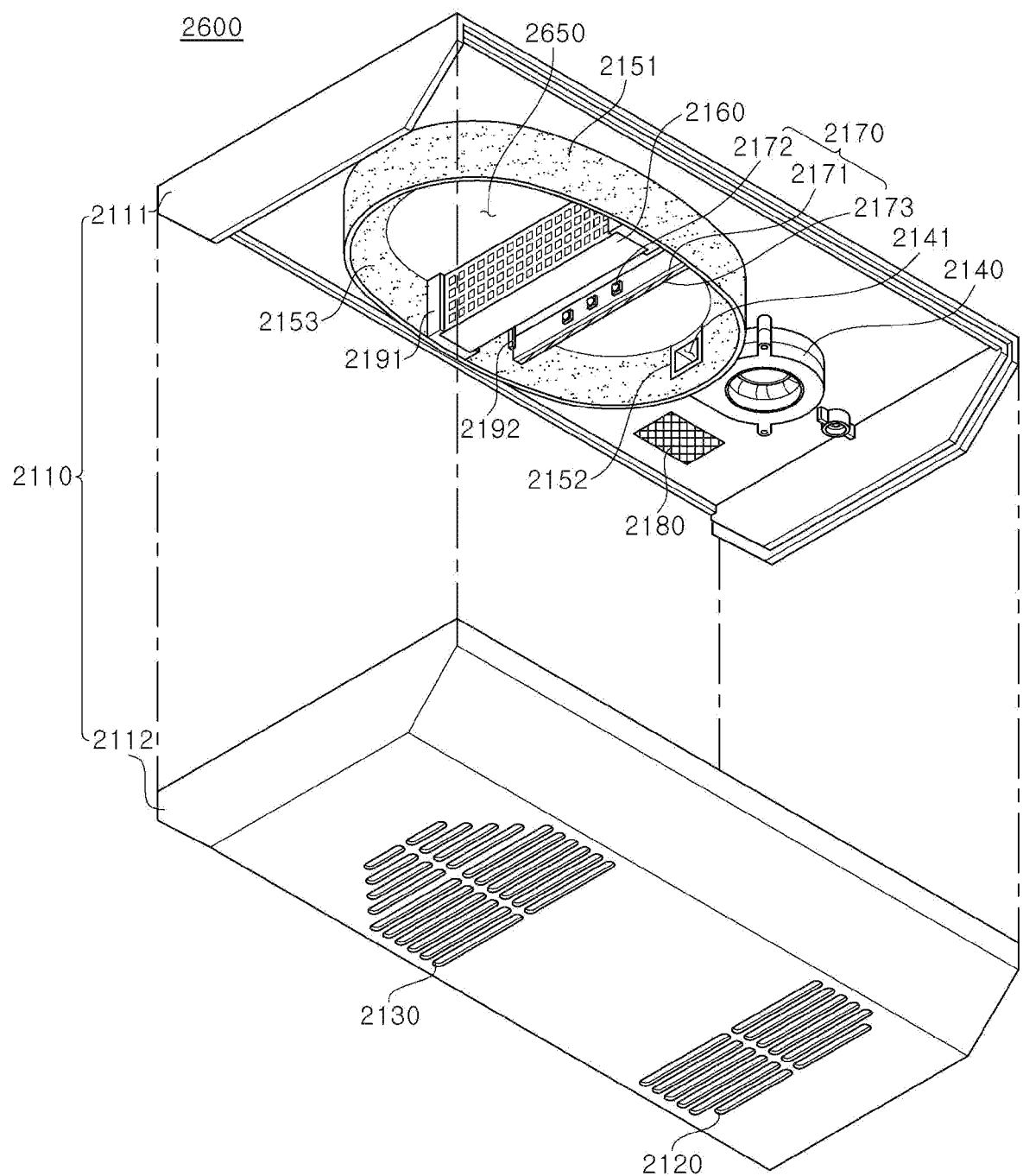
Figure 28:
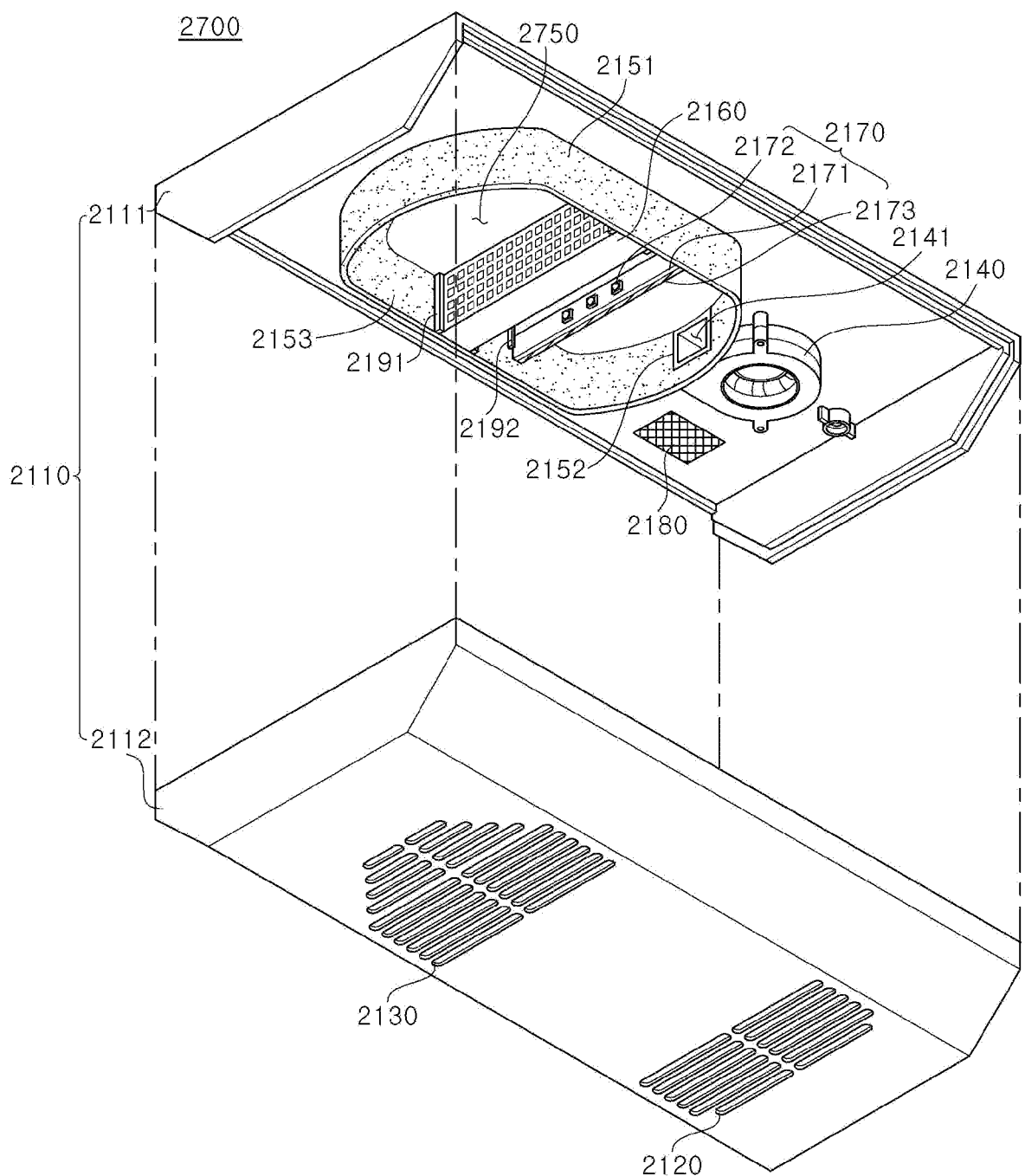

FIG. 26 to FIG. 28 are exemplary views of deodorization modules including flow paths according to exemplary embodiments of the disclosure, respectively.

Flow paths shown in FIG. 26 to FIG. 28 have different shapes than the flow paths of the deodorization modules according to the eighth to tenth exemplary embodiments. However, except for the shape of the flow path, the deodorization modules shown in FIG. 26 to FIG. 28 have the same internal structure as the deodorization modules according to the eighth to tenth exemplary embodiments. Thus, with regard to the deodorization modules shown in FIG. 26 to FIG. 28, detailed description of the same components as those of the deodorization modules according to the eighth to tenth exemplary embodiments will be omitted.

Referring to FIG. 26, a flow path 2550 of a deodorization module 2500 has a polygonal cross-section.

Referring to FIG. 27, a flow path 2650 of a deodorization module 2600 has an elliptical cross-section.

Referring to FIG. 28, a flow path 2750 of a deodorization module 2700 has a cross-sectional shape composed of two parallel straight lines and two curves connecting opposite ends of one straight line to opposite ends of the other straight line, respectively.

FIG. 26 to FIG. 28 are provided for illustration to show that the flow path of the deodorization module according to the disclosure may be formed in various shapes, as needed. That is, the shape of the flow path of the deodorization module is not limited to those shown in FIG. 21 to FIG. 28.

FIGS. 29 and 30 are exemplary views of a storage apparatus according to a second exemplary embodiment of the inventive concepts.

FIG. 29 is a front view of a storage apparatus according to a second exemplary embodiment of the inventive concepts. FIG. 30 is a side perspective view of the storage apparatus according to the second exemplary embodiment.

In this exemplary embodiment, the storage apparatus 2800 is a refrigerator. The storage apparatus 2800 includes a storage chamber 2810 and a deodorization module 2400.

The storage chamber 2810 has an internal space. Food is stored in the internal space of the storage chamber 2810.

In addition, the storage chamber 2810 is formed with a fastening groove 2820 for installation of the deodorization module 2400. The fastening groove 2820 is formed on an inner wall of the storage chamber 2810. Here, the fastening groove 2820 is shaped to receive the fastening member 2410 of the deodorization module 2400. That is, the fastening groove 2820 is shaped to receive the bent portion of the fastening member 2410 of the deodorization module 2400.

In this exemplary embodiment, the deodorization module 2400 may include plural fastening members 2410. For example, a fastening member 2410 formed at one side of the deodorization module 2400 may have a different shape than a fastening member 2410 formed at the other side of the deodorization module 2400. This makes it easy to insert the plural fastening members 2410 of the deodorization module 2400 into the respective fastening grooves 2820. Thus, all the fastening members 2410 of the deodorization module 2400 do not necessarily have the same shape. In addition, the fastening member 2410 may have any suitable shape, without limitation.

Further, the shape of the fastening groove 2820 of the storage chamber 2810 may vary depending on the shape of the fastening member 2410 of the deodorization module 2400.

Here, the deodorization module 2400 is the deodorization module according to the eleventh exemplary embodiment. Although the inventive concepts have been described using the deodorization module 2400 according to the eleventh exemplary embodiment as an example, it should be understood that the inventive concepts are not limited thereto. That is, the deodorization module may be any one of the deodorization modules shown in FIG. 21 to FIG. 28.

The deodorization module 2400 is mounted on the storage chamber 2810. Specifically, the deodorization module 2400 is mounted on the inner wall of the storage chamber 2810 by inserting the fastening member 2410 of the deodorization module 2400 into the fastening groove 2820.

In this exemplary embodiment, opposite side surfaces of the deodorization module 2400 are inclined toward one another. That is, the distance between opposite side surfaces of the cover 2112 of the deodorization module 2400 is gradually reduced from one side to the other side of the cover. Here, the other side of the cover is opposite the one side of the cover in a vertical direction. In FIG. 29, the one side of the cover is a top of the cover and the other side of the cover is a bottom of the cover. With this shape of the deodorization module 2400, the deodorization module 2400 can be installed in the storage chamber 2810 in as space-efficient a manner as possible.

In this exemplary embodiment, it has been described that the storage apparatus 2800 is a refrigerator. However, it should be understood that the inventive concepts are not limited thereto and the storage apparatus 2800 may be any apparatus storing food. For example, the storage apparatus 2800 may be a heating cabinet.

Although certain exemplary embodiments and implementations have been described herein, other embodiments and modifications will be apparent from this description. Accordingly, the inventive concepts are not limited to such embodiments, but rather to the broader scope of the appended claims and various obvious modifications and equivalent arrangements as would be apparent to a person of ordinary skill in the art.

What is claimed:

1. A sterilization module comprising:
    a housing including a bar fixed member and a substrate fixed member, and formed of a reflective material, wherein each of the bar fixed member and the substrate fixed member protrudes inward from an inner side surface of the housing and comprises a groove;
    a photocatalyst bar disposed such that air introduced into the housing passes through the photocatalyst bar;
    a light source module including a light source substrate and an ultraviolet (UV) light source disposed on a first surface of the light source substrate, wherein the light source module is configured to emit light toward the photocatalyst bar; and
    an external guide protruding outward around an outer periphery of the housing such that the external guide protrudes outward around an outer periphery of the housing to thereby hold the housing in place within the external guide,
    wherein the photocatalyst bar is secured in the housing by inserting a side surface of the photocatalyst bar into the groove of the bar fixed member,
    wherein the light source module is secured in the housing by inserting at least of a region of the light source substrate into the groove of the substrate fixed member,
    wherein the external guide is of a shape so as to enable only a first region of the sterilization module to be exposed to an external space of the housing and a second region of the sterilization module to not be exposed to an external space of the housing, and
    wherein an amount of the sterilization module that is not exposed to an external space of the housing is determined based on a distance from a lower surface of the sterilization module that the external guide is fitted around the outer periphery of the housing, to the external guide.

2. The sterilization module according to claim 1, wherein the housing has an upper surface and a lower surface that are substantially parallel to each other and that are separated from each other by a fixed distance,
    wherein the external guide is fitted around the outer periphery of the housing so as to be substantially parallel to the upper surface and the lower surface of the housing, and wherein based on whether the external guide that is fitted around the outer periphery of the housing is moved closer to the upper surface or the lower surface of the housing results in the first region and the second region of the sterilization module being adjustable.

3. The sterilization module according to claim 1, wherein the external guide is fitted around the outer periphery of the housing so as to be substantially parallel to an upper surface and a lower surface of the housing.

4. The sterilization module according to claim 1, wherein the photocatalyst bar comprises a plurality of through-holes.

5. The sterilization module according to claim 1, wherein the photocatalyst bar is disposed between the light source substrate and a discharge hole.

6. The sterilization module according to claim 1, wherein the photocatalyst bar is formed of at least one material of a ceramic and metal.

7. The sterilization module according to claim 1, wherein the light source module includes a plurality of UV light sources.

8. The sterilization module according to claim 1, wherein the light source module further includes a plate of metal material disposed on a second surface of the light source substrate.

9. The sterilization module according to claim 1, further comprising spaces disposed above and below the light source module.

10. The sterilization module according to claim 9, wherein the air introduced into the housing moves to the photocatalyst bar through the spaces disposed above and below the light source module.

11. The sterilization module according to claim 1, wherein the external guide is secured in an external component providing the external space of the housing.

12. The sterilization module according to claim 1, further including a control region for controlling the light source module.

13. The sterilization module according to claim 1, the bar fixed member and the substrate fixed member are formed separately from the housing.

14. A sterilization module comprising:
a housing including a bar fixed member and a substrate fixed member, and formed of a reflective material, wherein each of the bar fixed member and the substrate fixed member protrudes inward from an inner side surface of the housing and has a groove;
a photocatalyst bar disposed such that air introduced into the housing passes through the photocatalyst bar;
a light source module including a light source substrate and at least one ultraviolet (UV) light source on a first surface of the light source substrate, the light source module configured to emit light toward the photocatalyst bar; and
an external guide protruding outward around an outer periphery of the housing,
wherein the photocatalyst bar is secured in the housing by inserting a side surface of the photocatalyst bar into the groove of the bar fixed member,
wherein side surfaces of the photocatalyst bar contact inner side surfaces of the housing, respectively,
wherein the light source module is secured in the housing by inserting at least of a region of the light source substrate into the groove of the substrate fixed member,
wherein the sterilization module is secured in an external component providing an external space of the housing by the external guide,
wherein the external guide is of a shape so as to enable only a first region of the sterilization module to be exposed to an external space of the housing and a second region of the sterilization module to not be exposed to an external space of the housing,
wherein the external guide is fitted around the outer periphery of the housing so as to be substantially parallel to an upper surface and a lower surface of the housing, and
wherein an amount of the sterilization module that is not exposed to an external space of the housing is determined based on a distance from a lower surface of the sterilization module that the external guide is fitted around the outer periphery of the housing, to the external guide.

15. The sterilization module according to claim 14, wherein the housing has an upper surface and a lower surface that are substantially parallel to each other and that are separated from each other by a fixed distance,
wherein the external guide is fitted around the outer periphery of the housing so as to be substantially parallel to the upper surface and the lower surface of the housing, and
wherein based on whether the external guide that is fitted around the outer periphery of the housing is moved closer to the upper surface or the lower surface of the housing results in the first region and the second region of the sterilization module being adjustable.

16. The sterilization module according to claim 14, wherein the photocatalyst bar is formed of at least one material of a ceramic and metal.

17. The sterilization module according to claim 14, wherein the light source module further includes a plate of metal material disposed on a second surface of the light source substrate.

18. The sterilization module according to claim 14, including:
spaces disposed above and below the light source module, and
wherein the air introduced into the housing moves to the photocatalyst bar through the spaces disposed above and below the light source module.

19. The sterilization module according to claim 14, further including a control region for controlling the light source module.

* * * * *